United States Patent
Nagaoka et al.

(10) Patent No.: US 9,837,620 B2
(45) Date of Patent: Dec. 5, 2017

(54) BENZOPYRIDOINDOLE DERIVATIVE AND ORGANIC ELECTROLUMINESCENT ELEMENT

(71) Applicant: HODOGAYA CHEMICAL CO., LTD., Tokyo (JP)

(72) Inventors: Makoto Nagaoka, Tokyo (JP); Kouki Kase, Tokyo (JP); Shigeru Kusano, Tokyo (JP); Teruaki Koizumi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 115 days.

(21) Appl. No.: 14/913,774

(22) PCT Filed: Sep. 1, 2014

(86) PCT No.: PCT/JP2014/072899
§ 371 (c)(1),
(2) Date: Feb. 23, 2016

(87) PCT Pub. No.: WO2015/033883
PCT Pub. Date: Mar. 12, 2015

(65) Prior Publication Data
US 2016/0254458 A1    Sep. 1, 2016

(30) Foreign Application Priority Data

Sep. 9, 2013    (JP) .................. 2013-185841

(51) Int. Cl.
*H01L 51/00*    (2006.01)
*C07D 471/14*   (2006.01)
(Continued)

(52) U.S. Cl.
CPC ........ *H01L 51/0072* (2013.01); *C07D 471/04* (2013.01); *C09K 11/06* (2013.01);
(Continued)

(58) Field of Classification Search
CPC .. H01L 51/0072; C07D 471/14; C07D 471/22
(Continued)

(56) References Cited

U.S. PATENT DOCUMENTS 5,639,914 A    6/1997    Tomiyama et al.
5,707,747 A    1/1998    Tomiyama et al.
(Continued)

FOREIGN PATENT DOCUMENTS

JP    8-48656    2/1996
JP    2734341    1/1998
(Continued)

OTHER PUBLICATIONS

Akehiko Iwaki et al., "Novek synthetic strategy of carbolines via palladium-catalyzed amination an arylation reaction", J. Chem. Soc., Perkin Trans. 1, 1999, pp. 1505.
(Continued)

*Primary Examiner* — Vu A Nguyen
(74) *Attorney, Agent, or Firm* — Greenblum & Bernstein, P.L.C.

(57) ABSTRACT

According to the present invention, there are provided a benzopyridoindole derivative represented by the following general formula (1); and an organic EL element including a pair of electrodes and at least one organic layer sandwiched therebetween, wherein the above derivative is used as a constituent material for the at least one organic layer. The benzopyridoindole derivative of the present invention is excellent in electron injection/transport performance, has hole blocking capability, is highly stable in a thin film state, and excels in various characteristics. Thus, it is useful as a material for an organic EL element with a high efficiency, a low driving voltage, and high durability.

(Continued)

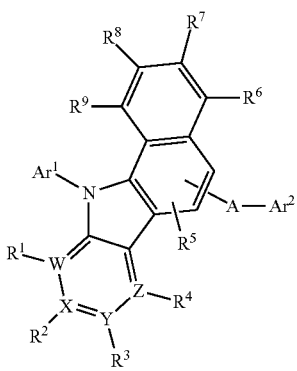

12 Claims, 2 Drawing Sheets

(51) Int. Cl.
*C07D 471/22* (2006.01)
*C07D 471/04* (2006.01)
*C09K 11/06* (2006.01)
*H01L 51/50* (2006.01)

(52) U.S. Cl.
CPC ...... *H01L 51/0052* (2013.01); *H01L 51/0058* (2013.01); *H01L 51/50* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5012* (2013.01); *H01L 51/5072* (2013.01); *H01L 51/5092* (2013.01); *H01L 51/5096* (2013.01)

(58) Field of Classification Search
USPC ............................................. 428/690
See application file for complete search history.

(56) References Cited

U.S. PATENT DOCUMENTS

| | | |
|---|---|---|
| 5,792,557 A | 8/1998 | Nakaya et al. |
| 5,869,199 A | 2/1999 | Kido |
| 6,878,469 B2 | 4/2005 | Yoon et al. |
| 2011/0175079 A1 | 7/2011 | Yokoyama et al. |
| 2013/0341604 A1 | 12/2013 | Yokoyama et al. |

FOREIGN PATENT DOCUMENTS

| | | | | |
|---|---|---|---|---|
| JP | 11-144867 | 5/1999 | | |
| JP | 3194657 | 6/2001 | | |
| JP | 2006-66580 | 3/2006 | | |
| JP | 2006066580 A | * 3/2006 | ............ | H01L 51/00 |
| JP | 2012-521414 | 9/2012 | | |
| KR | 10-2011-0014752 | 2/2011 | | |
| KR | DE 102013214399 | * 1/2014 | ......... | H01L 51/0071 |
| KR | 10-2014-0082273 | 7/2014 | | |
| WO | 03/060956 | 7/2003 | | |
| WO | 2010/035723 | 4/2010 | | |
| WO | 2010/110553 | 9/2010 | | |
| WO | 2013/032297 | 3/2013 | | |

OTHER PUBLICATIONS

Tatsuo Ishiyama et al., "Palladium (0)-Catalyzed Cross-Coupling Reaction of Alkoxydiboron with Haloarenes: A Direct Procedure for Arylboronic Esters", J. Org. Chem, 60, 1995, pp. 7508.

N. Miyaura et al., "The Palladium-Catalyzed Cross-Coupling Reaction of Phenylboronic Acid With Haloarenes in the Presence of Bases", Synthetic Communications, 11 (7), 1981, pp. 513.

International Search Report issued ind PCT/JP2014/072899, dated Sep. 30, 2014.

* cited by examiner

9: CATHODE
8: ELECTRON INJECTION LAYER
7: ELECTRON TRANSPORT LAYER
6: HOLE BLOCKING LAYER
5: LIGHT EMISSION LAYER
4: HOLE TRANSPORT LAYER
3: HOLE INJECTION LAYER
2: TRANSPARENT ANODE
1: GLASS SUBSTRATE

BENZOPYRIDOINDOLE DERIVATIVE AND ORGANIC ELECTROLUMINESCENT ELEMENT

TECHNICAL FIELD

This invention relates to a compound suitable for an organic electroluminescent element, and the element. More specifically, the invention relates to a benzopyridoindole derivative, and an organic electroluminescent element using the derivative.

BACKGROUND ART

An organic electroluminescent element (may hereinafter be referred to as an organic EL element) is a self light-emitting element, and is thus brighter, better in visibility, and capable of clearer display, than a liquid crystal element. Hence, active researches have been conducted on organic EL elements.

In 1987, C. W. Tang et al. of Eastman Kodak developed a laminated structure element sharing various roles among different materials, thereby imparting practical applicability to organic EL elements using organic materials. They laminated a layer of a fluorophor capable of transporting electrons, and a layer of an organic substance capable of transporting holes, and injecting the charges of electrons and holes into the layer of the fluorophor to perform light emission, thereby obtaining a high luminance of 1,000 cd/m$^2$ or more at a voltage of 10V or less (see Patent Document 1 and Patent Document 2).

Many improvements have been made to date for commercialization of organic EL elements. For example, high efficiency and durability are achieved by an electroluminescent element sharing the various roles among more types of materials, and having a positive electrode, a hole injection layer, a hole transport layer, a light emission layer, an electron transport layer, an electron injection layer, and a negative electrode provided in sequence on a substrate.

For a further increase in the luminous efficiency, it has been attempted to utilize triplet excitons, and the utilization of phosphorescent light emitting compounds has been considered.

Furthermore, elements utilizing light emission by thermally activated delayed fluorescence (TADF) have been developed. An external quantum efficiency of 5.3% has been realized by an element using a thermally activated delayed fluorescence material.

The light emission layer can also be prepared by doping a charge transporting compound, generally called a host material, with a fluorescent compound, a phosphorescent light emitting compound, or a material radiating delayed fluorescence. The selection of the organic material in the organic EL element greatly affects the characteristics of the element, such as efficiency and durability.

With the organic EL element, the charges injected from both electrodes recombine in the light emission layer to obtain light emission, and how efficiently the charges of the holes and the electrons are passed on to the light emission layer is of importance. Hole injecting properties are enhanced, and electron mobility is increased to increase the probability of holes and electrons recombining and, moreover, excitons generated within the light emission layer are confined, whereby a high luminous efficiency can be obtained. Thus, the role of the electron transport material is so important that there has been a desire for an electron transport material having high electron injection properties, allowing marked electron mobility, possessing high hole blocking properties, and having high durability to holes.

In connection with the life of the element, heat resistance and amorphism of the material are also important. A material with low thermal resistance is thermally decomposed even at a low temperature by heat produced during element driving, and the material deteriorates. In a material with low amorphism, crystallization of a thin film occurs even in a short time, and the element deteriorates. Thus, high resistance to heat and satisfactory amorphism are required of the material to be used.

A representative light emitting material, tris (8-hydroxyquinoline)aluminum (will hereinafter be abbreviated as Alq$_3$), is generally used as an electron transport material as well. However, the work function of Alq$_3$ is 5.8 eV, and cannot be said to have hole blocking performance.

As a measure for preventing some of the holes from passing through the light emission layer and increasing the probability of charge recombination in the light emission layer, there is a method of inserting a hole blocking layer. As hole blocking materials, triazole derivatives (see Patent Document 3), bathocuproine (will hereinafter be abbreviated as BCP), and aluminum-mixed ligand complexes {for example, aluminum (III) bis (2-methyl-8-quinolinato)-4-phenylphenolate (will hereinafter be abbreviated as BAlq)} have so far been proposed.

As an electron transport material excellent in hole blocking properties, 3-(4-biphenylyl)-4-phenyl-5-(4-t-butylphenyl)-1,2,4-triazole (will hereinafter be abbreviated as TAZ) has been proposed (see Patent Document 3).

TAZ has a great work function of 6.6 eV, indicating a high hole blocking ability. Thus, when used as an electron-transporting hole blocking layer, to be laminated on the negative electrode side, for a fluorescent light emitting layer or a phosphorescent light emitting layer which are prepared, for example, by vacuum deposition or coating, TAZ contributes to an increase in the efficiency of the organic EL element.

Low electron transporting properties, however, are a major problem with TAZ, and there is need to combine TAZ with an electron transport material having higher electron transporting properties, thereby preparing an organic EL element.

BCP also has a work function as great as 6.7 eV, and has a high hole blocking ability. However, its glass transition point (Tg) is so low (83° C.) that its thin film is scarcely stable, and BCP cannot be said to function fully as a hole blocking layer.

In short, all the above materials are either lacking in film stability, or insufficient in the function of blocking holes. In order to improve the element characteristics of the organic EL element, there has been a desire for an organic compound excellent in electron injection/transport performance and hole blocking capability and highly stable in a thin film state.

As a compound improved in such defects, a compound having a benzopyridoindole ring structure has been proposed (see Patent Document 4).

However, an element using the compound of Patent Document 4 for an electron injection layer and/or an electron transport layer has been improved in luminous efficiency, but the improvement has been still insufficient. Thus, an even lower driving voltage, an even higher luminous efficiency and, in particular, an even higher current efficiency, have been desired.

PRIOR ART DOCUMENTS

Patent Documents

Patent Document 1: JP-A-Hei 8-48656
Patent Document 2: Japanese Patent No. 3194657
Patent Document 3: Japanese Patent No. 2734341
Patent Document 4: JP-A-2006-66580
Patent Document 5: WO2003/060956

Non-Patent Documents

Non-Patent Document 1: J. Chem. Soc., Perkin Trans. 1, 1505 (1999)
Non-Patent Document 2: J. Org. Chem., 60, 7508 (1995)
Non-Patent Document 3: Synth. Commun., 11, 513 (1981)

SUMMARY OF THE INVENTION

Problems to be Solved by the Invention

It is an object of the present invention to provide an organic compound, which is excellent in electron injection/transport performance, has hole blocking capability, is highly stable in a thin film state, and excels in various characteristics, as a material for a high efficiency, high durability organic EL element.

It is another object of the present invention to provide an organic EL element having high efficiency, low driving voltage, and high durability with the use of this compound.

Means for Solving the Problems

To attain the above objects, the present inventors paid attention to the facts that a benzopyridoindole ring structure had high ability to transport electrons, and that this structure was excellent in heat resistance. Based on these facts, they designed and chemically synthesized a compound having a benzopyridoindole ring structure. Using this compound, moreover, they experimentally produced various organic EL elements, and extensively evaluated the characteristics of the elements. As a result, they have accomplished the present invention.

According to the present invention, there is provided a benzopyridoindole derivative represented by the following general formula (1)

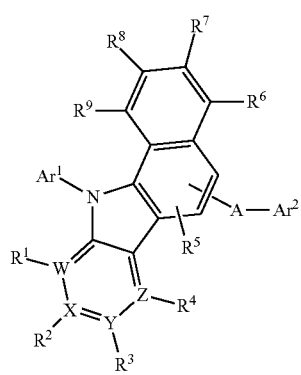

(1)

where
A represents a single bond, a divalent group of an aromatic hydrocarbon, a divalent group of an aromatic heterocycle, or a divalent group of a condensed polycyclic aromatic, $Ar^1$ and $Ar^2$ may be the same or different, and each represent an aromatic hydrocarbon group, an aromatic heterocyclic group, or a condensed polycyclic aromatic group, $R^1$ to $R^9$ may be the same or different, and each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group, W, X, Y and Z each represent a carbon atom or a nitrogen atom, and only one of W, X, Y and Z is a nitrogen atom, and this nitrogen atom does not have the hydrogen atom of $R^1$ to $R^4$ or a substituent.

For the benzopyridoindole derivative of the present invention, the following embodiments are preferred:

(A) The benzopyridoindole derivative is a benzopyridoindole derivative represented by the following general formula (1-1):

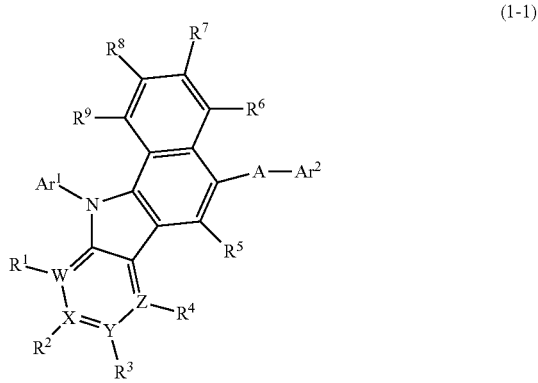

(1-1)

wherein,
A, $Ar^1$, $Ar^2$, $R^1$ to $R^9$, W, X, Y and Z have the same meanings as those defined for the aforementioned general formula (1).

(B) A is a single bond.
(C) A is a divalent group of an aromatic hydrocarbon having one or two rings, or a divalent group of naphthalene.
(D) $Ar^2$ is an aromatic hydrocarbon group having 3 or more rings, or a tri- or higher cyclic condensed polycyclic aromatic group.
(E) $Ar^2$ is an anthracenyl group having a substituent.
(F) $Ar^1$ is an unsubstituted phenyl group.

According to the present invention, moreover, there is provided an organic EL element including a pair of electrodes and at least one organic layer sandwiched therebetween, wherein the above-mentioned benzopyridoindole derivative is used as a constituent material for the at least one organic layer.

In the organic EL element of the present invention, it is preferred that the organic layer be an electron transport layer, a hole blocking layer, a light emission layer, or an electron injection layer.

Effects of the Invention

The benzopyridoindole derivative of the present invention has the following physical properties:
(1) Electron injection characteristics are satisfactory.
(2) Electron transfer rate is high.
(3) Hole blocking capability is excellent.

(4) Thin film state is stable.
(5) Heat resistance is excellent.

Moreover, the organic EL element of the present invention has the following properties:
(6) Luminous efficiency and power efficiency are high.
(7) Light emission starting voltage is low.
(8) Practical driving voltage is low.
(9) Durability is excellent.

The benzopyridoindole derivative of the present invention can be used, for example, as a constituent material for the electron injection layer and/or the electron transport layer of the organic EL element. The use of the benzopyridoindole derivative of the present invention, which has high electron injection and moving speeds as compared with conventional materials, as an electron injection layer and/or an electron transport layer obtains the following effects:
(a) The efficiency of electron transport from the electron transport layer into the light emission layer is increased.
(b) Luminous efficiency is increased.
(c) Driving voltage is lowered, and durability of the organic EL element is enhanced.

The benzopyridoindole derivative of the present invention can also be used as a constituent material for the hole blocking layer of the organic EL element. By using the benzopyridoindole derivative of the present invention, which has excellent ability to block holes, is better in electron transporting properties than conventional materials, and is highly stable in a thin film state, as a hole blocking layer, the following effects are obtained:
(d) A high luminous efficiency is exhibited.
(e) Driving voltage is lowered.
(f) Current resistance is improved, and the maximum light emission luminance of the organic EL element is increased.

Furthermore, the benzopyridoindole derivative of the present invention is also usable as a constituent material for the light emission layer of the organic EL element. The benzopyridoindole derivative of the present invention has excellent electron transport properties, and has a wide bandgap, as compared with conventional materials. By using such a benzopyridoindole derivative as a host material of the light emission layer, and supporting a fluorescence emitting substance or a phosphorescence emitting substance, called a dopant, in the host material to form the light emission layer, the following effects are obtained:
(g) Driving voltage is decreased.
(h) Luminous efficiency is increased.

That is, the organic EL element of the present invention uses a benzopyridoindole derivative which is higher in electron injecting properties, greater in mobility, better in hole blocking capability, more stable to holes, and more stable in a thin film state, than conventional electron transport materials. Thus, this organic EL element can confine excitons generated within the light emission layer, and can further increase the probability of recombination of holes and electrons to obtain a high luminous efficiency, and can lower driving voltage to realize high durability.

MODE FOR CARRYING OUT THE INVENTION

Figure 1:
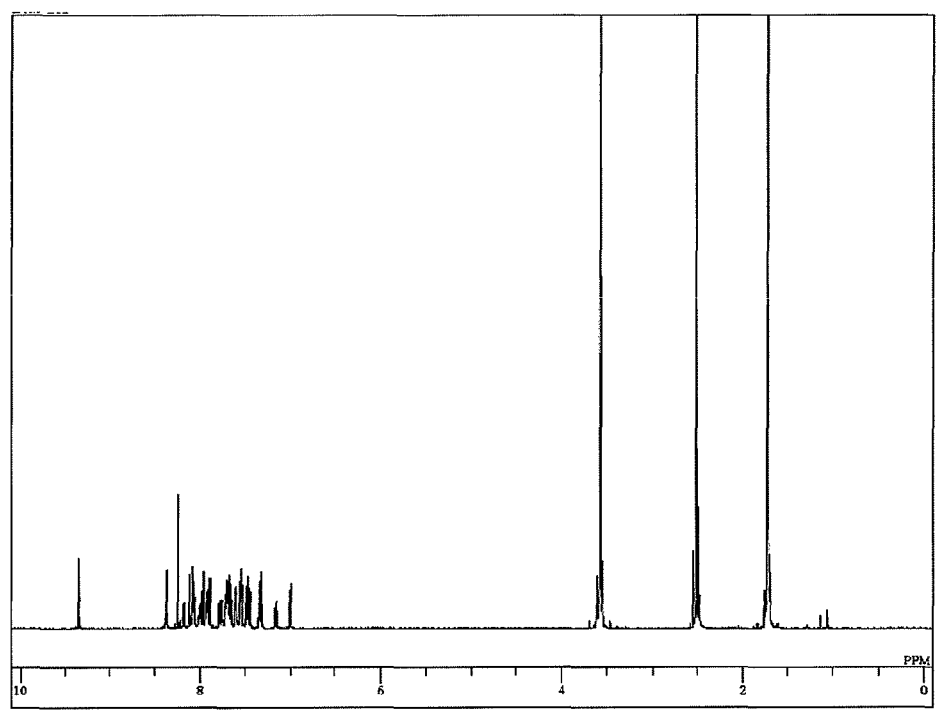
[FIG. 1] is a $^1$H-NMR chart diagram of the compound of Example 1 (Compound 3).

The novel benzopyridoindole derivative of the present invention is represented by the following general formula (1), and has a benzopyridoindole ring as its basic skeleton.

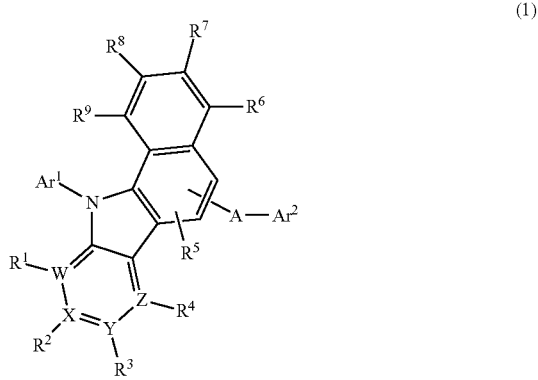

(1)

In the benzopyridoindole derivative represented by the above general formula (1), it is preferred that -A-Ar$^2$ be bonded at the para-position with respect to the nitrogen atom in the benzene ring of the indole ring. Such an embodiment is represented by the following general formula (1-1):

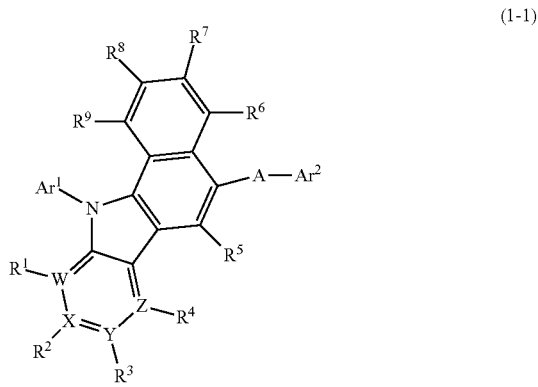

(1-1)

<A>

In the above general formula (1) or (1-1), A represents a single bond, a divalent group of an aromatic hydrocarbon, a divalent group of an aromatic heterocycle, or a divalent group of a condensed polycyclic aromatic. Examples of the aromatic hydrocarbon, aromatic heterocycle or condensed polycyclic aromatic are benzene, biphenyl, terphenyl, tetrakisphenyl, styrene, naphthalene, anthracene, acenaphthylene, fluorene, phenanthrene, indane, pyrene, triphenylene, fluoranthene, benzofluoranthene, chrysene, pyridine, pyrimidine, triazine, furan, pyrrole, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, acridine, bipyridine, and phenylpyridine.

The divalent group of the aromatic hydrocarbon, aromatic heterocycle, or condensed polycyclic aromatic, represented by A, is formed by removing two hydrogen atoms from the above-mentioned aromatic hydrocarbon, aromatic heterocycle, or condensed polycyclic aromatic. The aromatic hydrocarbon does not have a condensed polycyclic structure. The aromatic heterocycle, on the other hand, may be one having a condensed polycyclic structure.

The divalent group of the aromatic hydrocarbon, aromatic heterocycle, or condensed polycyclic aromatic, represented by A, may have a substituent. Examples of the substituent are:

a deuterium atom;

a cyano group;

a nitro group;

a halogen atom, for example, a fluorine atom or a chlorine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;

an alkyloxy group having 1 to 6 carbon atoms, for example, a methyloxy group, an ethyloxyl group, or a propyloxy group;

an alkenyl group, for example, an allyl group;

an aryloxy group, for example, a phenyloxy group or a tolyloxy group;

an arylalkyloxy group, for example, a benzyloxy group or a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a tetrakisphenyl, a styryl group, an acenaphthenyl group, or a phenylnaphthyl group;

an aromatic heterocyclic group, for example, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group, a triazinyl group, a pyrimidinyl group, a naphthyridinyl group, a phenanthrolinyl group, or an acridinyl group;

an arylvinyl group, for example, a styryl group or a naphthylvinyl group; and an acyl group, for example, an acetyl group or a benzoyl group.

Of the above substituents, the alkyl group having 1 to 6 carbon atoms or the alkyloxy group having 1 to 6 carbon atoms may be straight-chain or branched.

The above substituents maybe further substituted by the above exemplary substituent. Moreover, the substituents may bind to each other via a single bond, a substituted or unsubstituted methylene group, an oxygen atom, or a sulfur atom to form a ring.

<$Ar^1$, $Ar^2$>

In the general formula (1) or (1-1), $Ar^1$ and $Ar^2$ may be the same or different, and each represent an aromatic hydrocarbon group, an aromatic heterocyclic group, or a condensed polycyclic aromatic group.

The aromatic hydrocarbon group, the aromatic heterocyclic group, or the condensed polycyclic aromatic group, represented by $Ar^1$ or $Ar^2$, can be exemplified by a phenyl group, a biphenylyl group, a terphenylyl group, a tetrakisphenyl group, a styryl group, a naphthyl group, an anthracenyl group, an acenaphthenyl group, a phenanthrenyl group, a triphenylenyl group, a fluorenyl group, an indenyl group, a pyrenyl group, a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, a chrysenyl group, a fluoranthenyl group, and a benzofluoranthenyl group.

The aromatic hydrocarbon group, the aromatic heterocyclic group, or the condensed polycyclic aromatic group, represented by $Ar^1$ or $Ar^2$, may have a substituent. The substituent can be exemplified by the same substituents as those illustrated as the substituents that may be possessed by the divalent group of the aromatic hydrocarbon, aromatic heterocycle, or condensed polycyclic aromatic represented by A. The same holds true of the feasible embodiments for the substituents.

<$R^1$ to $R^9$>

In the general formula (1) or (1-1), $R^1$ to $R^9$ may be the same or different, and each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group.

The alkyl group having 1 to 6 carbon atoms, represented by $R^1$ to $R^9$, can be exemplified by a methyl group, an ethyl group, an n-propyl group, an isopropyl group, an n-butyl group, a 2-methylpropyl group, a tert-butyl group, an n-pentyl group, a 3-methylbutyl group, a tert-pentyl group, an n-hexyl group, an iso-hexyl group, and a tert-hexyl group. The alkyl group having 1 to 6 carbon atoms may be straight-chain or branched.

The aromatic hydrocarbon group, the aromatic heterocyclic group, or the condensed polycyclic aromatic group, represented by $R^1$ to $R^9$, can be exemplified by the same groups as those illustrated as the aforementioned aromatic hydrocarbon group, aromatic heterocyclic group, or condensed polycyclic aromatic group in connection with $Ar^1$ and $Ar^2$.

The aromatic hydrocarbon group, the aromatic heterocyclic group, or the condensed polycyclic aromatic group, represented by $R^1$ to $R^9$, may have a substituent. The substituent can be exemplified by the same ones as those illustrated as the substituents optionally possessed by the divalent group of the aromatic hydrocarbon, aromatic heterocycle, or condensed polycyclic aromatic represented by A. The same holds true of the feasible embodiments for the substituents.

<W, X, Y, Z>

In the general formula (1) or (1-1), W, X, Y and Z each represent a carbon atom or a nitrogen atom, and only one of W, X, Y and Z is a nitrogen atom (the remaining three being carbon atoms). When one of W, X, Y and Z is a nitrogen atom, this nitrogen atom shall not have the hydrogen atom of any of $R^1$ to $R^4$ or a substituent. That is, when W is a nitrogen atom, $R^1$ does not exist; when X is a nitrogen atom, $R^2$ does not exist; when Y is a nitrogen atom, $R^3$ does not exist; or when Z is a nitrogen atom, $R^4$ does not exist.

<Preferred Groups>

In the benzopyridoindole derivative represented by the general formula (1) or (1-1), a divalent group of an aromatic hydrocarbon having one or two rings, a divalent group of an aromatic heterocycle having one or two rings, a divalent group of naphthalene, or a single bond is preferred as A. Examples of the aromatic hydrocarbon having one or two rings, and the aromatic heterocycle having one or two rings are benzene, biphenyl, styrene, indane, pyridine, pyrimidine, triazine, furan, pyrrole, thiophene, quinoline, isoquinoline, benzofuran, benzothiophene, indoline, benzoxazole, benzothiazole, quinoxaline, benzimidazole, pyrazole, naphthyridine, bipyridine, and phenylpyridine. Further, as A, a divalent group of the aromatic hydrocarbon having one or two rings, a divalent group of naphthalene, or a single bond is preferred; a divalent group formed by removing two hydrogen atoms from benzene, biphenyl or naphthalene, or a single bond is more preferred; and a divalent group formed by removing two hydrogen atoms from benzene or biphenyl, or a single bond is particularly preferred.

As $Ar^1$, an aromatic hydrocarbon group, a condensed polycyclic aromatic group, or a sulfur-containing aromatic heterocycle such as a dibenzothienyl group, or an oxygen-containing aromatic heterocycle such as a dibenzofuranyl group is preferred; a phenyl group is more preferred from the viewpoint of the bipolarity of a compound; and an unsubstituted phenyl group is particularly preferred.

As $Ar^2$, an aromatic hydrocarbon group having 3 or more rings, an aromatic heterocyclic group having 3 or more rings, or a tri- or higher cyclic condensed polycyclic aromatic group is preferred. Examples of the aromatic hydrocarbon group having 3 or more rings, the aromatic heterocyclic group having 3 or more rings, or the tri- or higher cyclic condensed polycyclic aromatic group are a terphenylyl group, a tetrakisphenyl group, an anthracenyl group, an acenaphthenyl group, a phenanthrenyl group, a triphenylenyl group, a fluorenyl group, a pyrenyl group, a carbazolyl group, a dibenzofuranyl group, a dibenzothienyl group, a phenanthrolinyl group, an acridinyl group, a chrysenyl group, a fluoranthenyl group, and a benzofluoranthenyl group.

Furthermore, from the viewpoint of imparting a bias of charge to the benzopyridoindole derivative, as $Ar^2$, the aromatic hydrocarbon group having 3 or more rings, the tri- or higher cyclic condensed polycyclic aromatic group, or a dibenzothienyl group, a carbazolyl group, a phenanthrolinyl group, or a dibenzofuranyl group is preferred; the aromatic hydrocarbon group having 3 or more rings, or the tri- or higher cyclic condensed polycyclic aromatic group is more preferred; and an anthracenyl group is particularly preferred. The anthracenyl group may be unsubstituted or may have a substituent, but preferably has a substituent.

The substituent that $Ar^2$ may have is an aromatic hydrocarbon group, a condensed polycyclic aromatic group, or an aromatic heterocyclic group. Its preferred examples are a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a pyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, or an acridinyl group. Its more preferred examples are a phenyl group, a biphenylyl group, a naphthyl group, a phenanthrenyl group, a fluorenyl group, a pyridyl group, a triazinyl group, a pyrimidinyl group, a quinolyl group, an isoquinolyl group, a dibenzofuranyl group, and a dibenzothienyl group. From the viewpoint of imparting a bias of charge to the benzopyridoindole derivative, a phenyl group and a naphthyl group are particularly preferred.

As $R^1$ to $R^9$, an alkyl group having 1 to 6 carbon atoms, or a hydrogen atom is preferred, and hydrogen atoms as all of them are particularly preferred, because this will facilitate synthesis.

Of W, X, Y and Z, Y being a nitrogen atom is preferred.

As will be understood from the above-mentioned preferred groups represented by A, $Ar^1$, $Ar^2$, $R^1$ to $R^9$, W, X, Y and Z, a derivative, which has a structure having a plurality of nitrogen atoms on one side, and has a structure composed of only carbon atoms and nitrogen atoms on the other side, namely, a derivative having an asymmetric structure, is particularly preferred as the benzopyridoindole derivative of the present invention. In such a derivative, a bias occurs in its electrical charges. When the organic layer in the organic EL element, in particular, the electron transport layer, the hole blocking layer or the electron injection layer, is formed using such a derivative, therefore, the resulting organic EL element exhibits excellent characteristics.

<Manufacturing Method>

The benzopyridoindole derivative of the present invention can be synthesized, for example, by the following manufacturing method: A benzopyridoindole derivative having a structure corresponding to $R^1$ to $R^9$ which the desired benzopyridoindole derivative has (may hereinafter be referred to as "a benzopyridoindole derivative having $R^1$ to $R^9$") is provided, and the 11-position of such an benzopyridoindole derivative is substituted by an aryl group. Then, its 5-position is brominated, and the resulting bromine-substituted product is subjected to a cross-coupling reaction, such as Suzuki coupling, with a boronic acid or boronic ester having a structure corresponding to -A-$Ar^2$ which the desired benzopyridoindole derivative has, whereby the target product can be synthesized.

The benzopyridoindole derivative having $R^1$ to $R^9$ can be synthesized, for example, by performing the cyclization reaction of a halogenonaphthylaminopyridine, which has a structure corresponding to $R^1$ to $R^9$ present in the desired benzopyridoindole derivative, with the use of a palladium catalyst (see Non-Patent Document 1).

The arylation at the 11-position can be performed, for example, by a condensation reaction, such as Ullmann reaction or Buchwald-Hartwig reaction, between the benzopyridoindole derivative having $R^1$ to $R^9$ and a halide of an aromatic hydrocarbon compound, a condensed polycyclic aromatic compound or an aromatic heterocyclic compound.

The bromination at the 5-position can be performed, for example, by reacting the benzopyridoindole derivative, which has been substituted at the 11-position by an aryl group, with N-bromosuccinimide or the like. By changing a reagent and conditions for the bromination, a bromo-substituted product different in the position of substitution can be obtained.

The boronic acid or boronic ester used in the cross-coupling reaction, such as Suzuki coupling, can be synthesized by a known method (see Non-Patent Document 2). The concrete conditions and steps for the cross-coupling reaction such as Suzuki coupling are disclosed in Non-Patent Document 3.

The purification of the resulting compound can be performed, for example, by purification using a column chromatograph, adsorption purification using silica gel, activated carbon, activated clay or the like, recrystallization or crystallization using a solvent, or sublimation purification. Identification of the compound can be performed by NMR analysis. As physical property values, a melting point, a glass transition point (Tg) and a work function can be measured.

The melting point serves as an index to deposition properties. The glass transition point (Tg) serves as an index to stability in a thin film state. The melting point and the glass transition point (Tg) can be measured with a high sensitivity differential scanning calorimeter (DSC3100S, produced by Bruker AXS K.K.) using a powder.

The work function serves as an index to hole blocking capability. The work function can be measured by preparing a 100 nm thin film on an ITO substrate and using an ionization potential measuring device (PYS-202, produced by Sumitomo Heavy Industries, Ltd.) on the sample.

Of the benzopyridoindole derivatives of the present invention, concrete examples of the preferred compounds will be shown below, but the present invention is in no way limited to these compounds. Compound 1 is missing.

(Compound 2)

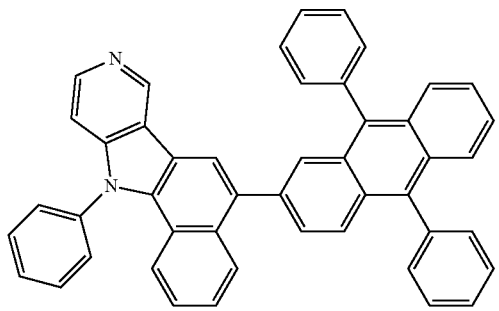

A = single bond
Y = nitrogen atom (Compound 3)

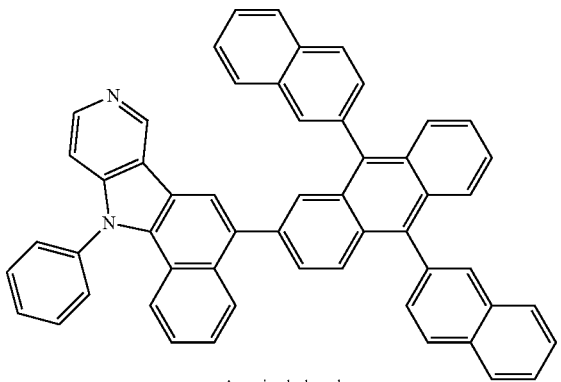

A = single bond
Y = nitrogen atom (Compound 4)

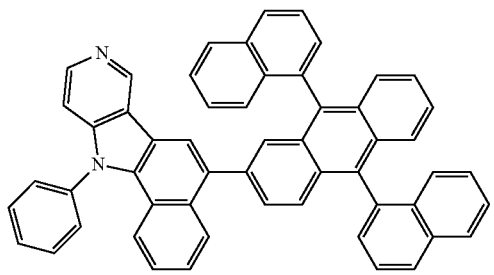

A = single bond
Y = nitrogen atom (Compound 5)

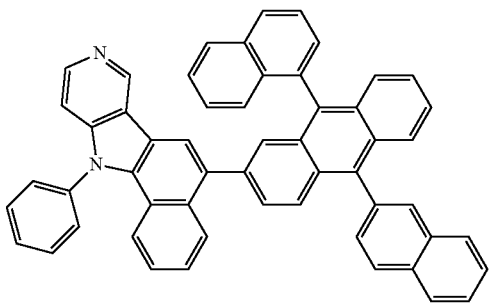

A = single bond
Y = nitrogen atom (Compound 6)

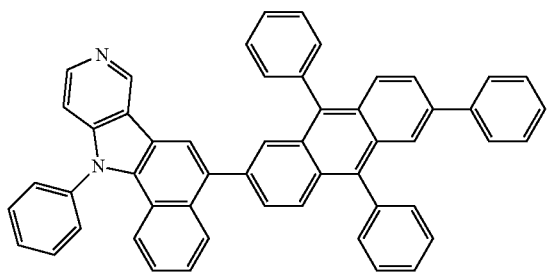

A = single bond
Y = nitrogen atom (Compound 7)

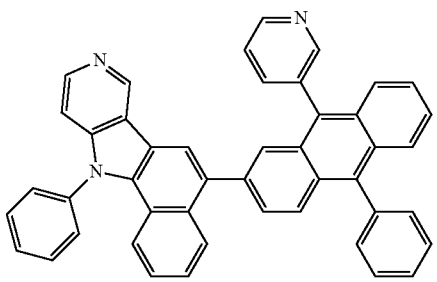

A = single bond
Y = nitrogen atom

-continued
(Compound 8)
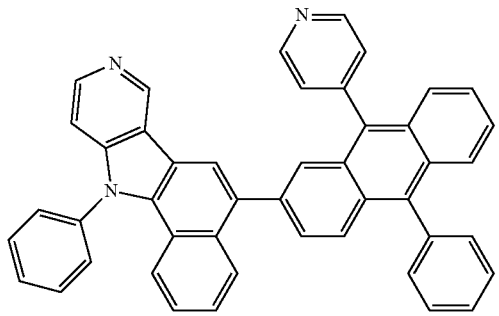
A = single bond
Y = nitrogen atom
(Compound 9)
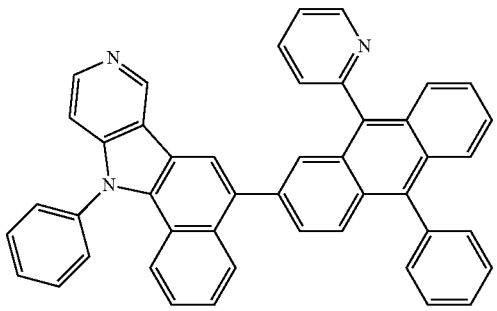
A = single bond
Y = nitrogen atom
(Compound 10)
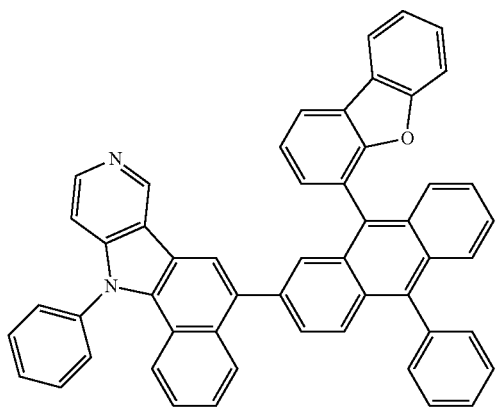
A = single bond
Y = nitrogen atom
(Compound 11)
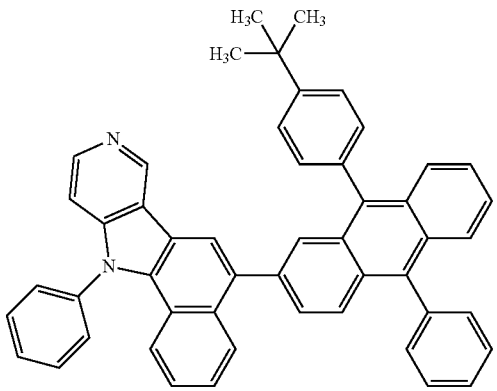
A = single bond
Y = nitrogen atom
(Compound 12)
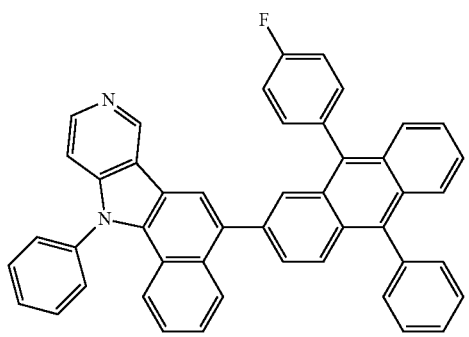
A = single bond
Y = nitrogen atom
(Compound 13)
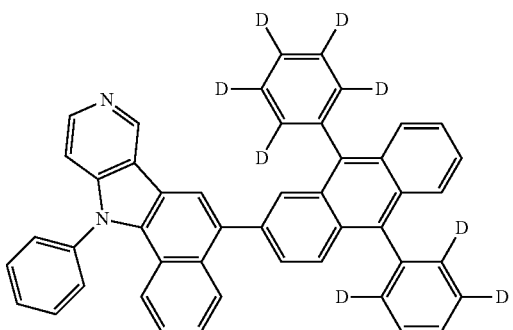
A = single bond
Y = nitrogen atom -continued
(Compound 14)
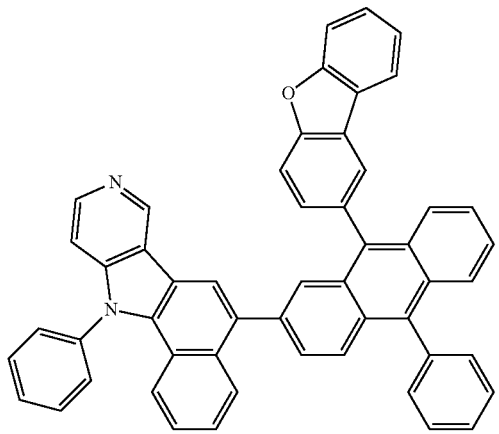
A = single bond
Y = nitrogen atom
(Compound 15)
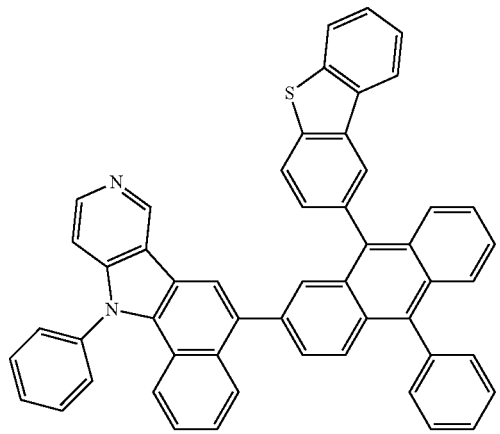
A = single bond
Y = nitrogen atom
(Compound 16)
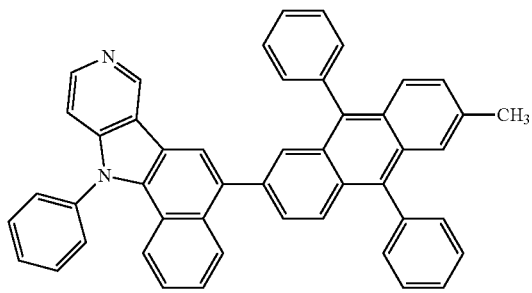
A = single bond
Y = nitrogen atom
(Compound 17)
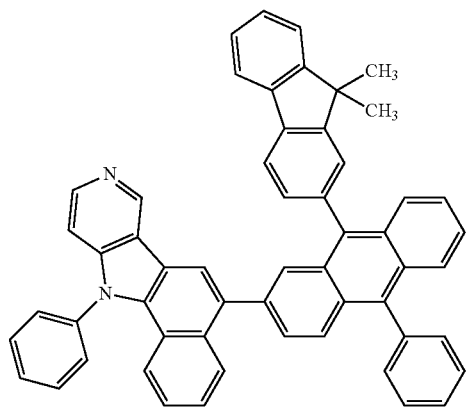
A = single bond
Y = nitrogen atom
(Compound 18)
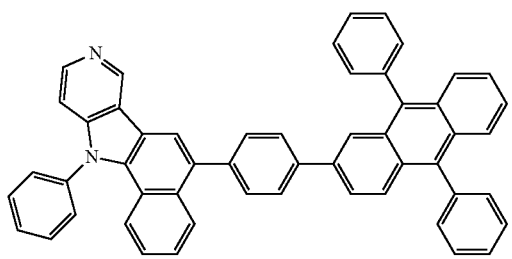
Y = nitrogen atom
(Compound 19)
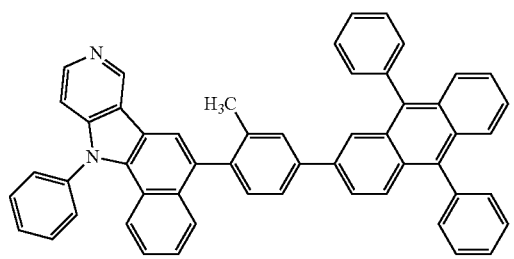
Y = nitrogen atom (Compound 20)
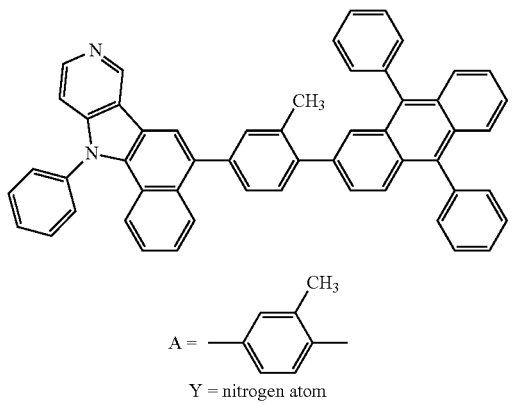
A = [2,5-dimethylphenyl structure with CH₃]
Y = nitrogen atom
(Compound 21)
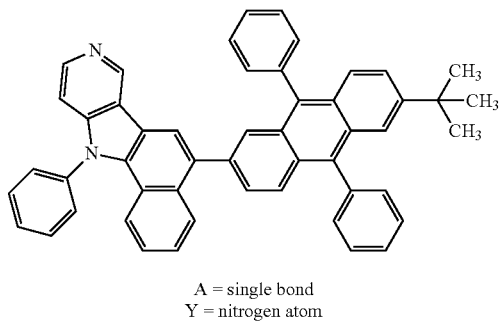
A = single bond
Y = nitrogen atom
(Compound 22)
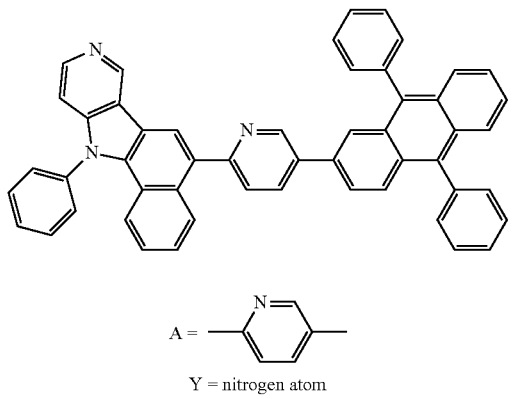
A = [pyridine structure]
Y = nitrogen atom
(Compound 23)
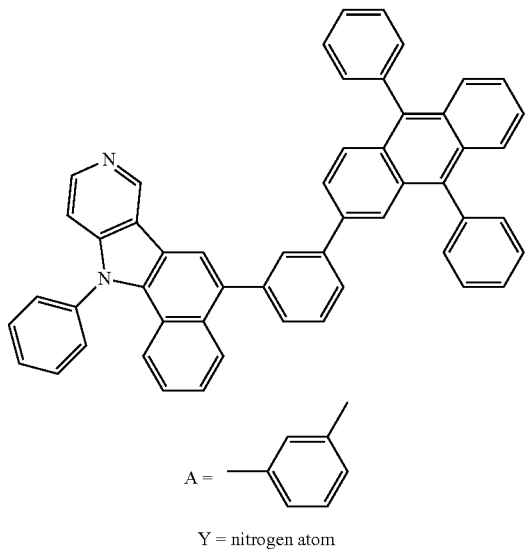
A = [meta-phenylene]
Y = nitrogen atom
(Compound 24)
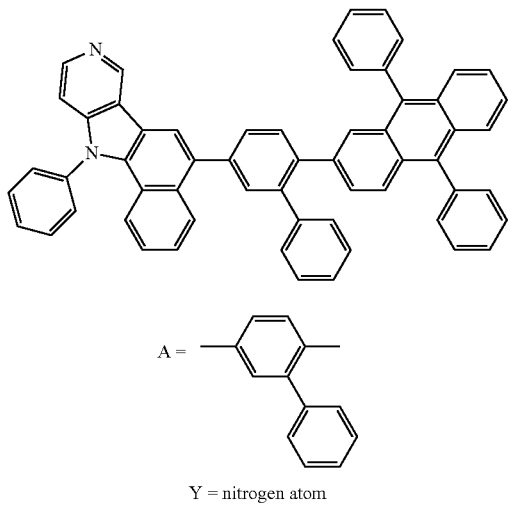
A = [biphenyl-methyl structure]
Y = nitrogen atom
(Compound 25)
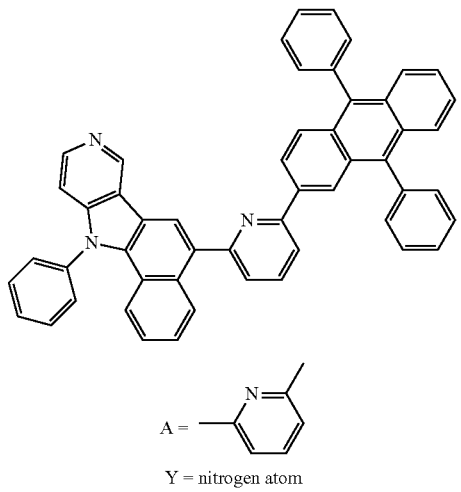
A = [pyridine structure]
Y = nitrogen atom (Compound 26)
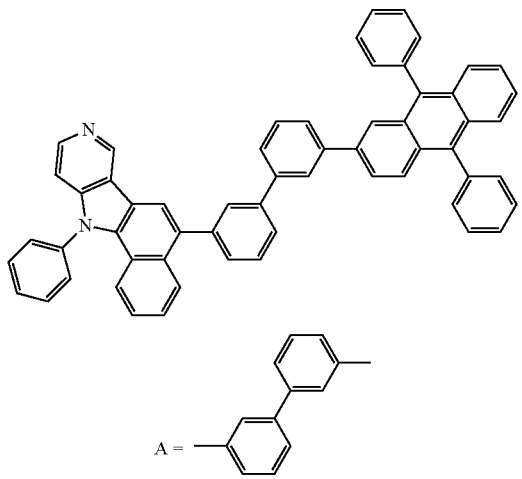
Y = nitrogen atom
(Compound 27)
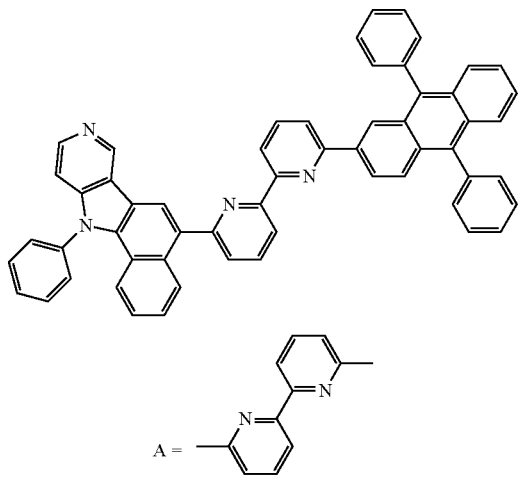
Y = nitrogen atom
(Compound 28)
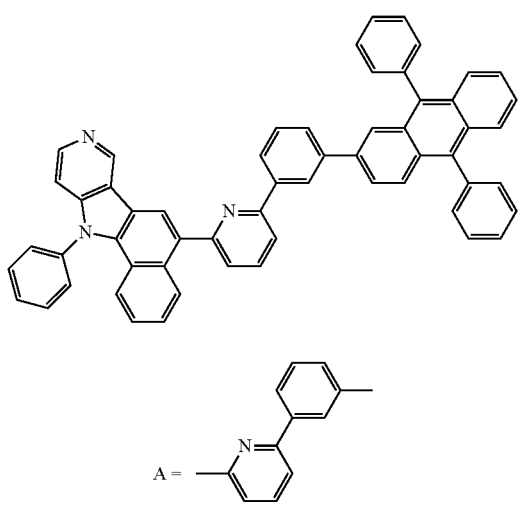
Y = nitrogen atom
(Compound 29)
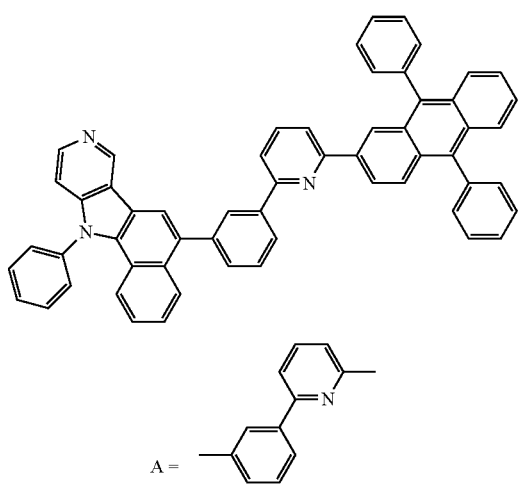
Y = nitrogen atom
(Compound 30)
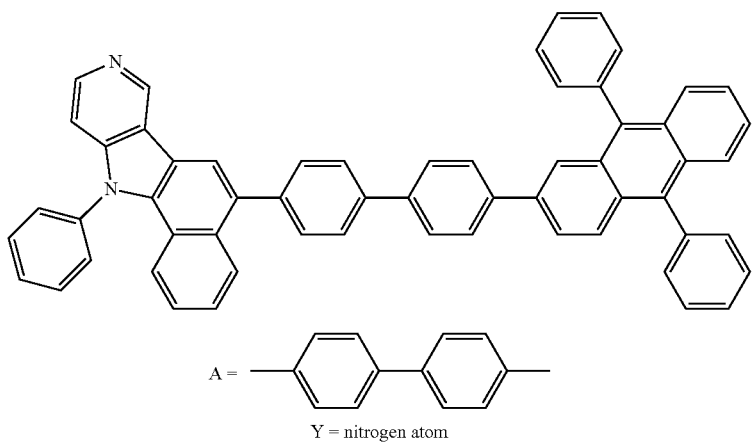
Y = nitrogen atom -continued
(Compound 31)
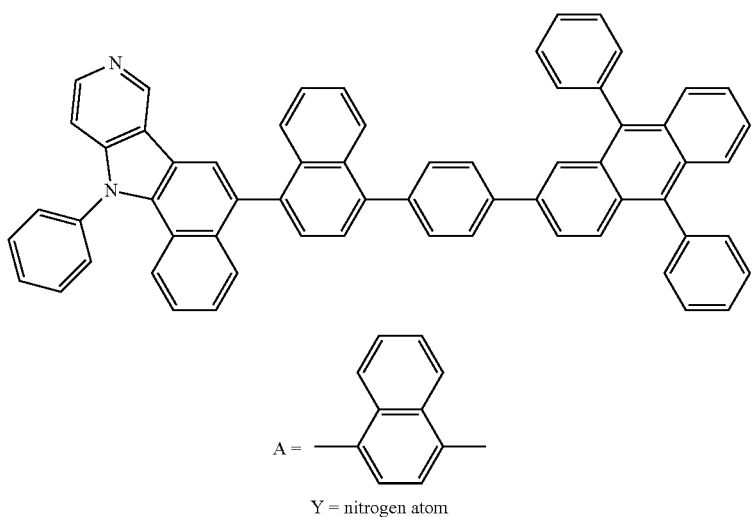
(Compound 32)
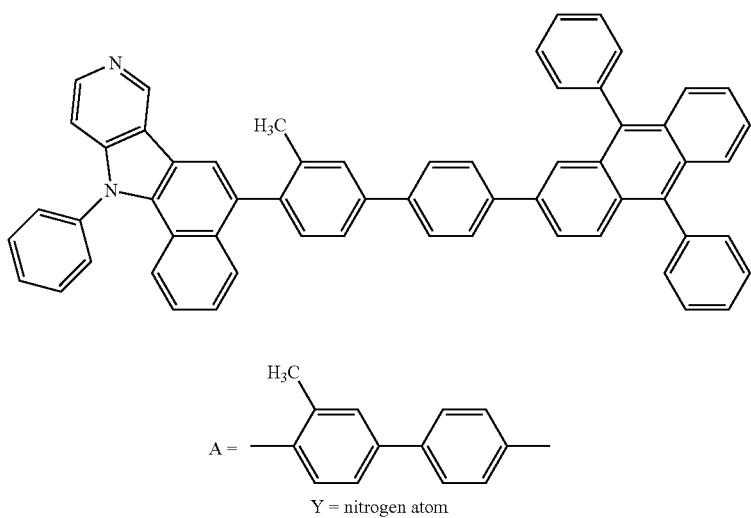
(Compound 33) (Compound 34)
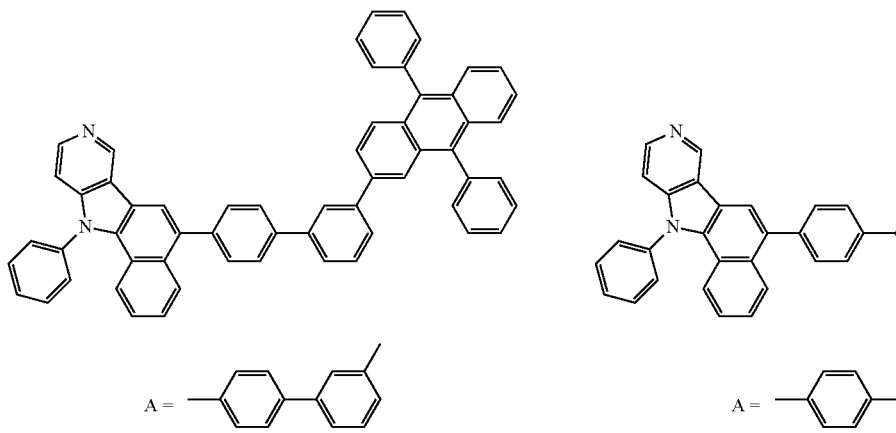

(Compound 35)
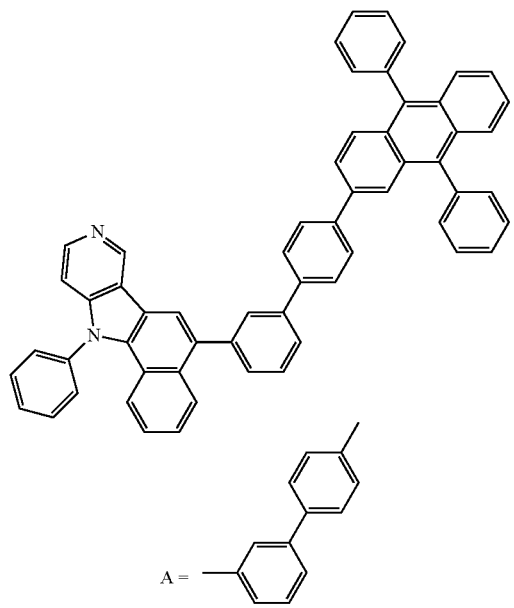
Y = nitrogen atom
(Compound 36)
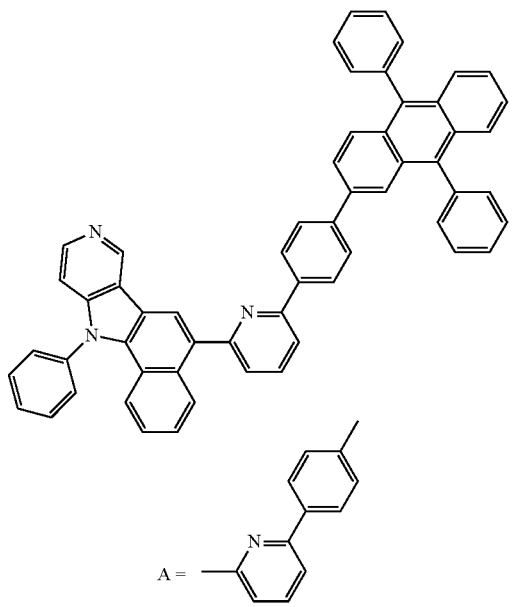
Y = nitrogen atom
(Compound 37)
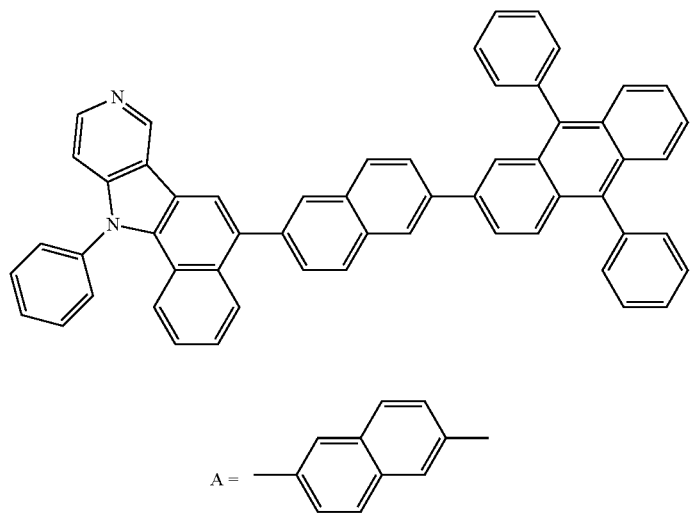
Y = nitrogen atom (Compound 38)
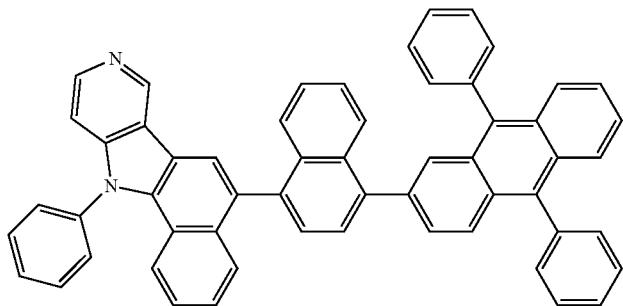
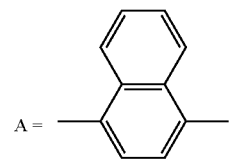
Y = nitrogen atom
(Compound 39)
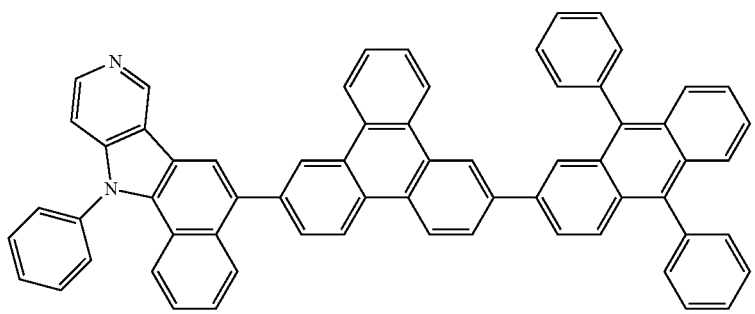
A = single bond
Y = nitrogen atom
(Compound 40)
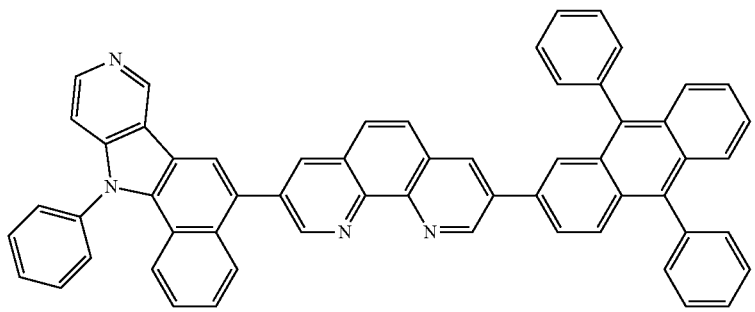
A = single bond
Y = nitrogen atom -continued
(Compound 41)
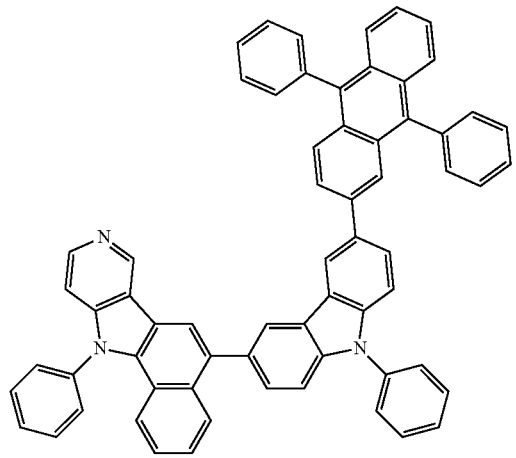
A = single bond
Y = nitrogen atom
(Compound 42)
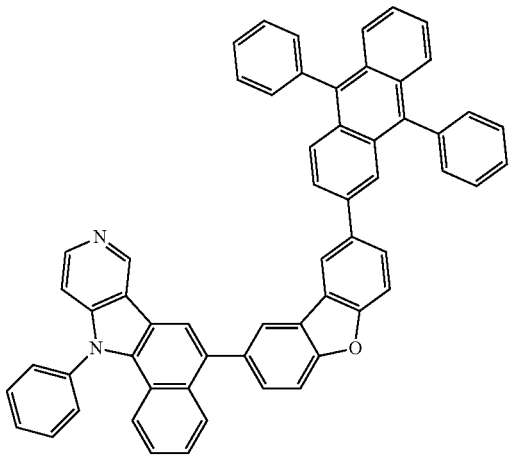
A = single bond
Y = nitrogen atom
(Compound 43)
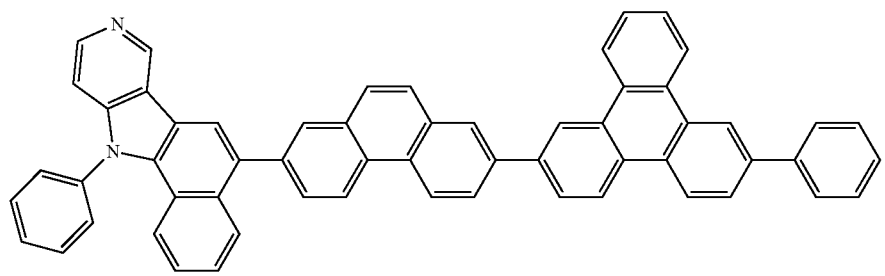
A = single bond
Y = nitrogen atom
(Compound 44)
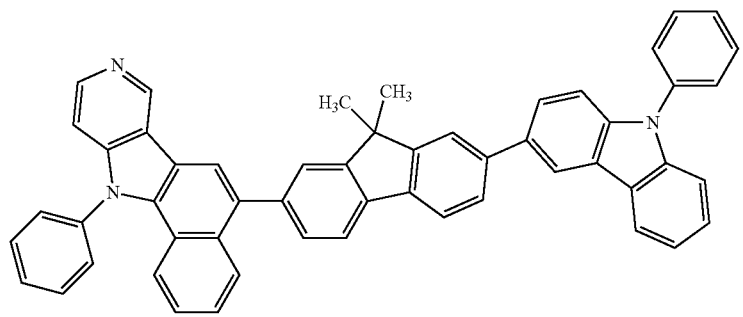
A = single bond
Y = nitrogen atom (Compound 45)
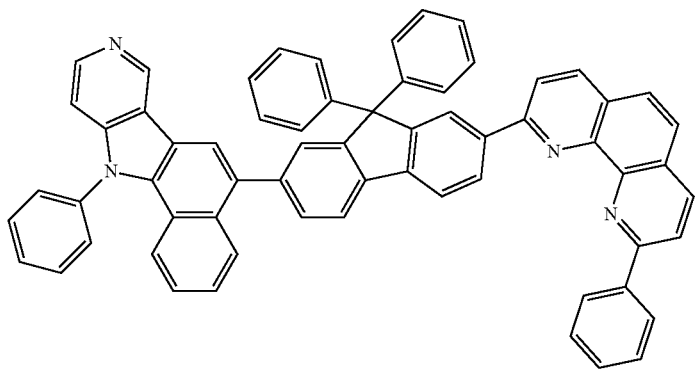
A = single bond
Y = nitrogen atom
(Compound 46)
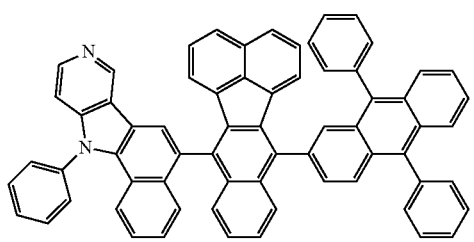
A = single bond
Y = nitrogen atom
(Compound 47)
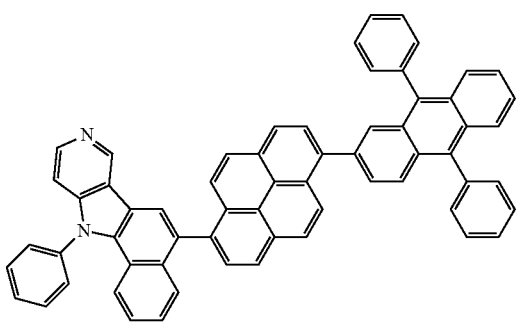
A = single bond
Y = nitrogen atom
(Compound 48)
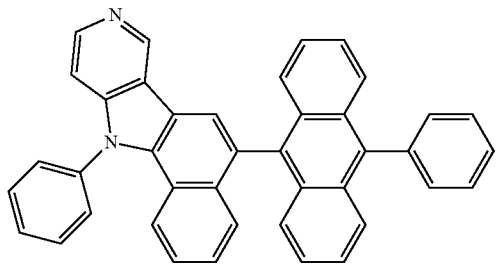
A = single bond
Y = nitrogen atom
(Compound 49)
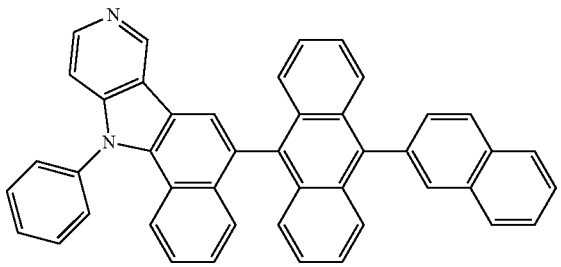
A = single bond
Y = nitrogen atom
(Compound 50)
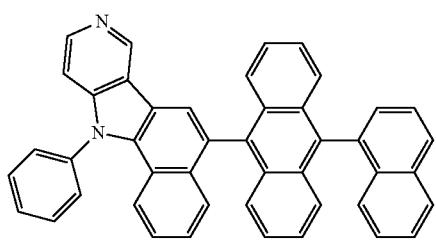
A = single bond
Y = nitrogen atom
(Compound 51)
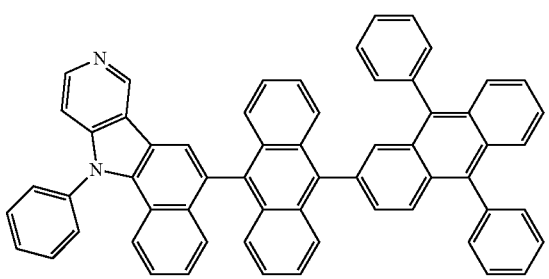
A = single bond
Y = nitrogen atom -continued
(Compound 52)
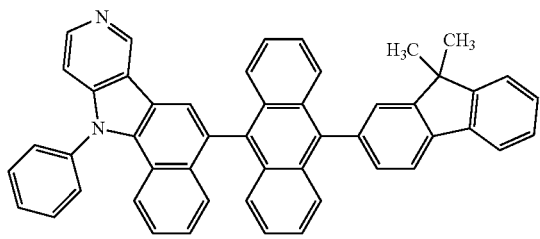
A = single bond
Y = nitrogen atom
(Compound 53)
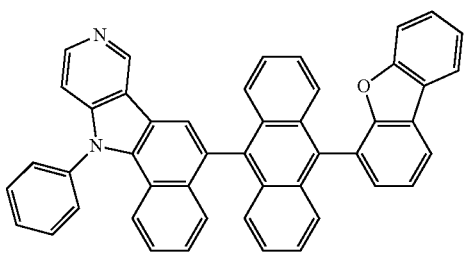
A = single bond
Y = nitrogen atom
(Compound 54)
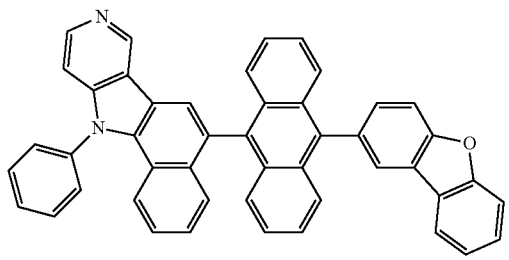
A = single bond
Y = nitrogen atom
(Compound 55)
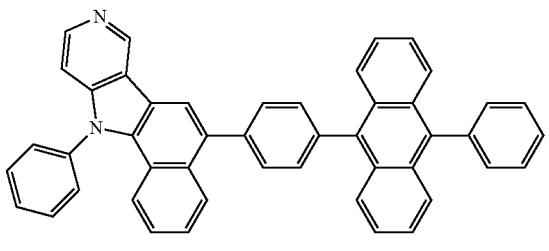
A = —⟨ ⟩—
Y = nitrogen atom
(Compound 56)
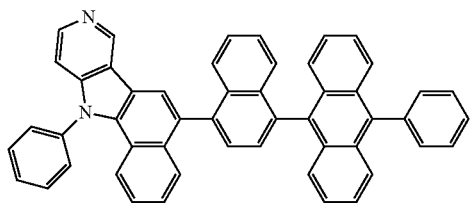
A =
Y = nitrogen atom
(Compound 57)
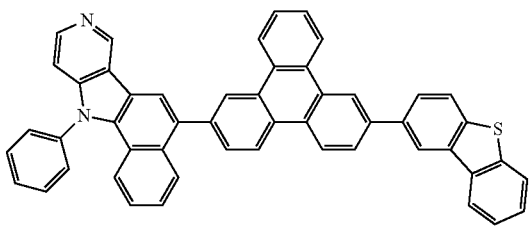
A = single bond
Y = nitrogen atom
(Compound 58)
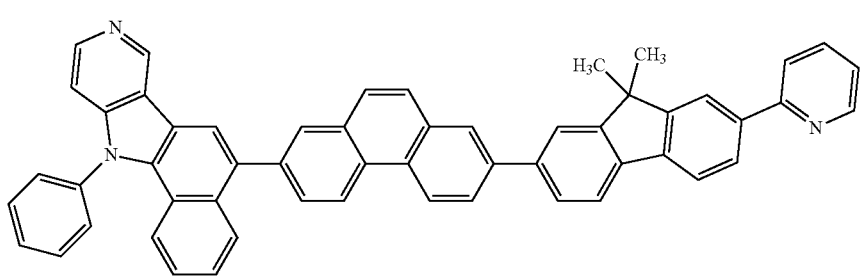
A = single bond
Y = nitrogen atom (Compound 59)
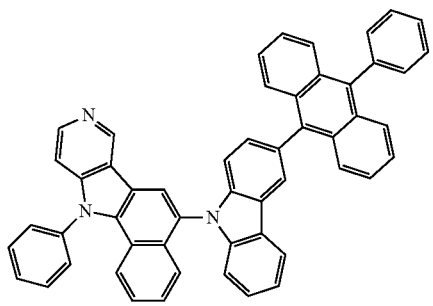
A = single bond
Y = nitrogen atom
(Compound 60)
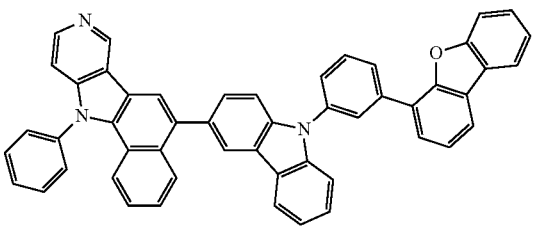
A = single bond
Y = nitrogen atom
(Compound 61)
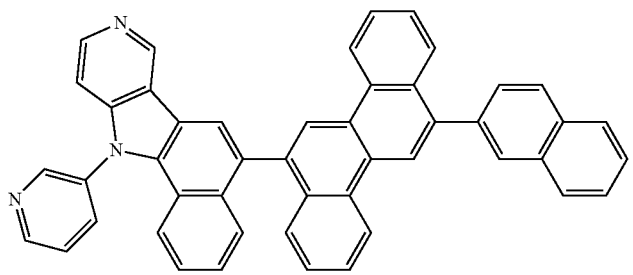
A = single bond
Y = nitrogen atom
(Compound 62)
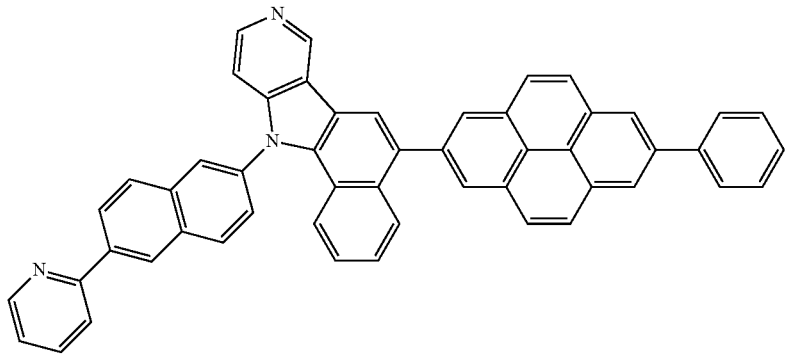
A = single bond
Y = nitrogen atom
(Compound 63)
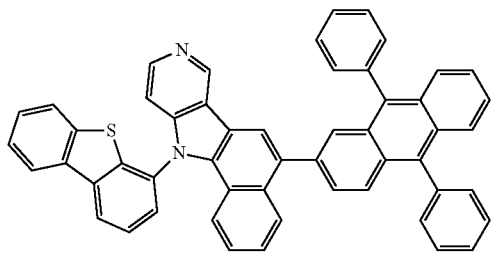
A = single bond
Y = nitrogen atom
(Compound 64)
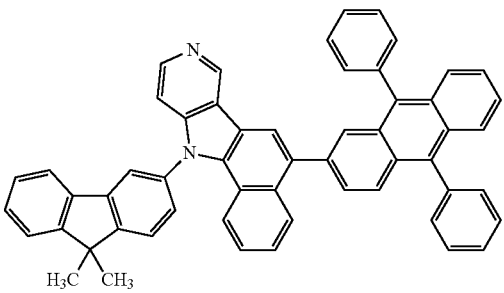
A = single bond
Y = nitrogen atom -continued
(Compound 65)
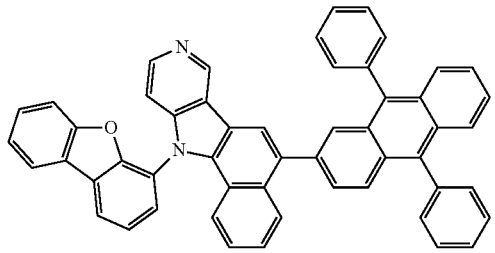
A = single bond
Y = nitrogen atom
(Compound 66)
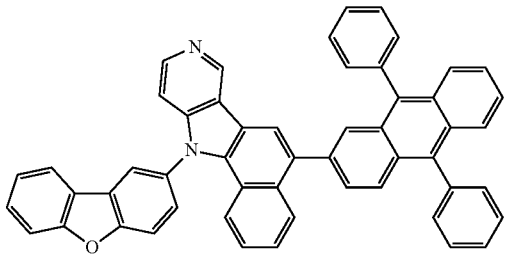
A = single bond
Y = nitrogen atom
(Compound 67)
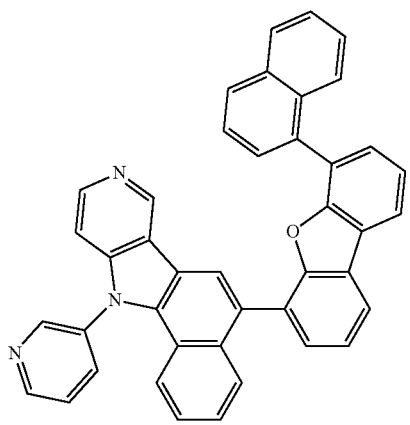
A = single bond
Y = nitrogen atom
(Compound 68)
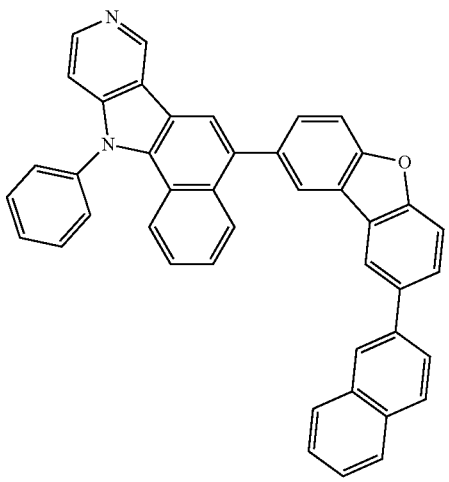
A = single bond
Y = nitrogen atom
(Compound 69)
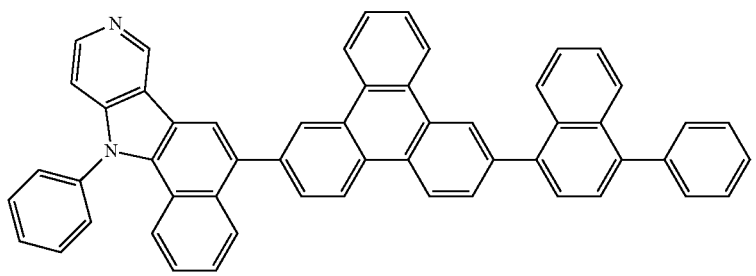
A = single bond
Y = nitrogen atom (Compound 70)
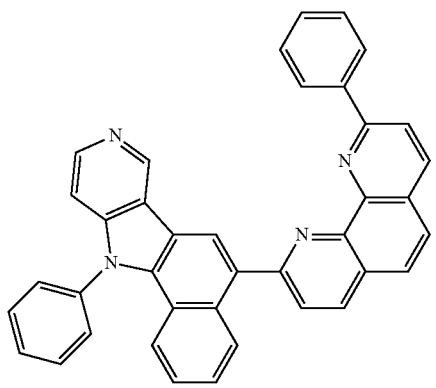
A = single bond
Y = nitrogen atom
(Compound 71)
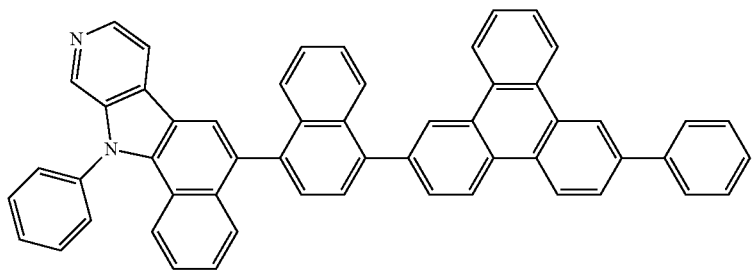
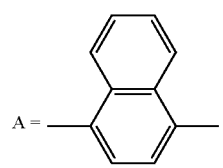
X = nitrogen atom
(Compound 72)
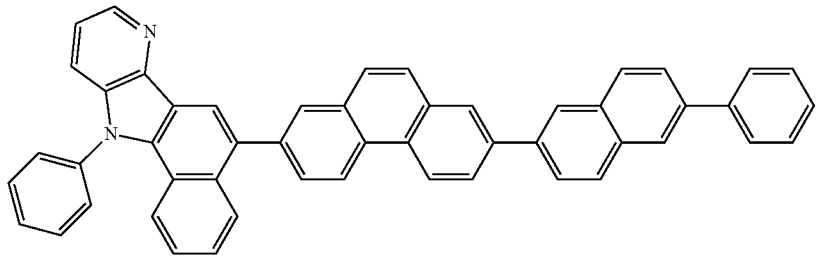
A = single bond
Z = nitrogen atom -continued
(Compound 73)
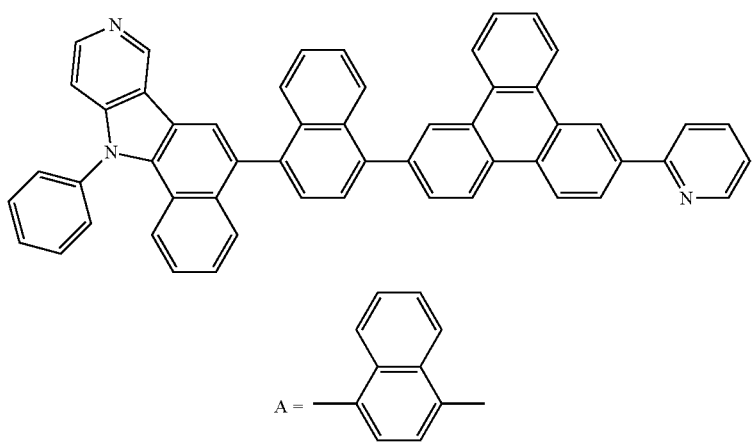
Y = nitrogen atom
(Compound 74)
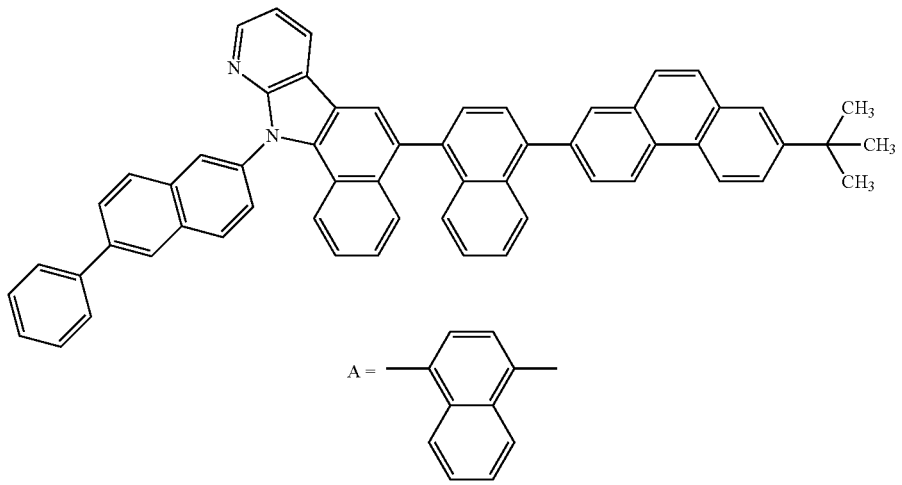
W = nitrogen atom
(Compound 75)
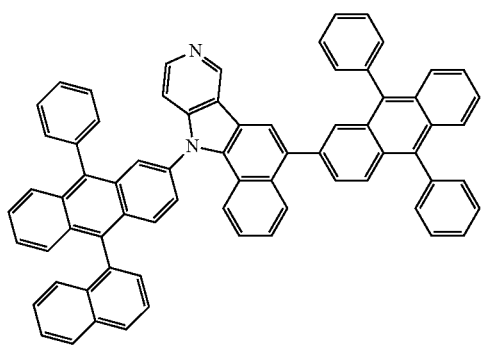
A = single bond
Y = nitrogen atom
(Compound 76)
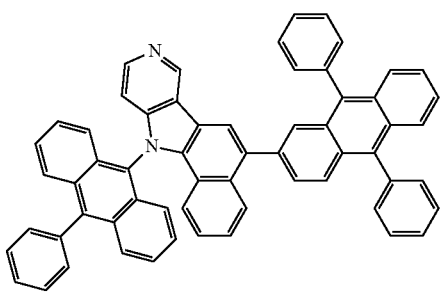
A = single bond
Y = nitrogen atom (Compound 77)

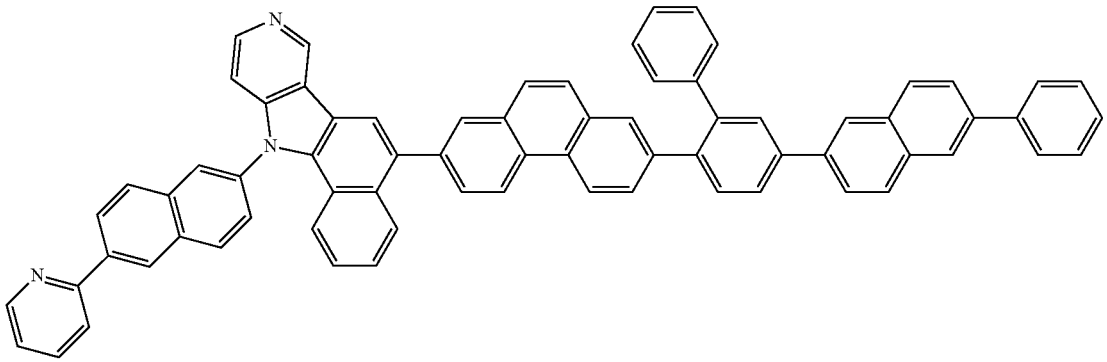

A = single bond
Y = nitrogen atom

<Organic EL Element>

Figure 3:
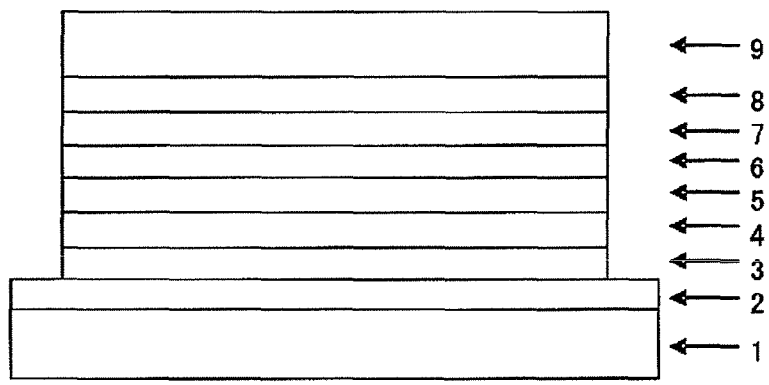
[FIG. 3] is a view showing the configuration of the EL elements of Examples 3, 4 and Comparative Example 1.

An organic EL element having organic layers formed using the benzopyridoindole derivative of the present invention described above (may hereinafter be referred to as the organic EL element of the present invention) has a layered structure, for example, as shown in FIG. 3. That is, in the organic EL element of the present invention, for example, a transparent anode 2, a hole injection layer 3, a hole transport layer 4, a light emission layer 5, a hole blocking layer 6, an electron transport layer 7, an electron injection layer 8, and a cathode 9 are provided in sequence on a substrate 1. The organic EL element of the present invention is not limited to such a structure, but for example, may have an electron blocking layer (not shown) between the light emission layer 5 and the hole transport layer 4. In this multilayer structure, some of the organic layers can be omitted. For example, there can be a configuration in which the hole injection layer 3 between the anode 2 and the hole transport layer 4, the hole blocking layer 6 between the light emission layer 5 and the electron transport layer 7, and the electron injection layer 8 between the electron transport layer 7 and the cathode 9 are omitted, and the anode 2, the hole transport layer 4, the light emission layer 5, the electron transport layer 7, and the cathode 9 are provided sequentially on the substrate 1.

The anode 2 may be composed of an electrode material publicly known per se and, for example, an electrode material having a great work function, such as ITO or gold, is used.

The hole injection layer 3 can be formed using a conventionally known hole injection material. Examples of the conventionally known hole injection material are as follows:

Porphyrin compounds typified by copper phthalocyanine;
Triphenylamine derivatives of starburst type;
Triphenylamine trimmers and tetramers, for example, arylamine compounds having in the molecule a structure in which 3 or more triphenylamine structures are coupled together by a single bond or a divalent group containing no hetero-atom;
Acceptor type heterocylic compounds, for example, hexacyanoazatriphenylene; and
Coating type polymeric materials.

The hole injection layer (thin film) can be formed by vapor deposition or any other publicly known method such as a spin coat method or an ink jet method. Various layers to be described below can be similarly formed as films by a publicly known method such as vapor deposition, spin coating, or ink jetting.

The hole transport layer 4 can be formed using a conventionally known hole transport material. The conventionally known hole transport material can be exemplified by the following: Benzidine derivatives, for example, N,N'-diphenyl-N, N'-di (m-tolyl)benzidine (hereinafter abbreviated as TPD), N,N'-diphenyl-N, N'-di (α-naphthyl)benzidine (hereinafter abbreviated as NPD), and N,N,N', N'-tetrabiphenylylbenzidine;

1,1-bis[(di-4-tolylamino)phenyl]cyclohexane (hereinafter abbreviated as TAPC); and Various triphenylamine trimers and tetramers. The above hole transport materials may be used singly for film formation, but may also be mixed with other materials for film formation. Alternatively, it is permissible to form a plurality of layers with the use of one or more of the above materials, and use a multilayer film composed of a stack of such layers as the hole transport layer.

In the present invention, moreover, it is also possible to form a layer concurrently serving as the hole injection layer 3 and the hole transport layer 4. Such a hole injection/transport layer can be formed using a coating type polymeric material such as poly(3,4-ethylenedioxythiophene) (hereinafter abbreviated as PEDOT)/poly (styrenesulfonate) (hereinafter abbreviated as PSS).

In forming the hole injection layer 3 (like the hole transport layer 4), the material usually used for this layer is further P-doped with trisbromophenylaminium hexachloroantimonate or the like and can be used for the layer, or a polymeric compound having the structure of a benzidine derivative such as TPD in its partial structure in addition to the usual material can also be used for the layer.

The electron blocking layer (not shown) can be formed using a publicly known electron blocking compound. The publicly known electron blocking compound can be exemplified by the following: Carbazole derivatives, for example, 4,4',4"-tri (N-carbazolyl)triphenylamine (hereinafter abbreviated as TCTA), 9,9-bis[4-(carbazol-9-yl) phenyl]fluorene, 1,3-bis(carbazol-9-yl)benzene (hereinafter abbreviated as mCP), and 2,2-bis(4-carbazol-9-ylphenyl)adamantane (hereinafter abbreviated as Ad-Cz); and Compounds having a triphenylsilyl group and a triarylamine structure, for example, 9-[4-(carbazol-9-yl)phenyl]-9-[4-(triphenylsilyl)phenyl]-9H-fluorene.

The electron blocking layer can be formed using one or more of the above publicly known materials. Alternatively, it is permissible to form a plurality of layers with the use of one or more of the above materials, and use a multilayer film composed of a stack of such layers as the electron blocking layer.

The light emission layer 5 can be formed, for example, using the following luminescent materials, in addition to the benzopyridoindole derivative of the present invention:

Metal complexes of quinolinol derivatives including $Alq_3$;
Various metal complexes;
Anthracene derivatives;
Bisstyrylbenzene derivatives;
Pyrene derivatives;
Oxazole derivatives; and
Polyparaphenylenevinylene derivatives.

The light emission layer 5 may be composed of a host material and a dopant material.

As the host material, thiazole derivatives, benzimidazole derivatives, and polydialkylfluorene derivatives can be used in addition to the benzopyridoindole derivative of the present invention and the above-mentioned luminescent materials.

Usable as the dopant material are, for example, quinacridone, coumarin, rubrene, perylene and derivatives thereof; benzopyran derivatives; rhodamine derivatives; and aminostyryl derivatives.

The light emission layer 5 can also be formed using one or more of the luminescent materials. The light emission layer 5 can be in a single-layer configuration, or have a multilayer structure composed of a plurality of layers stacked.

Furthermore, a phosphorescent light emitting material can be used as the luminescent material. As the phosphorescent light emitting material, a phosphorescence emitting substance in the form of a metal complex containing iridium, platinum or the like can be used. Concretely, a green phosphorescence emitting substance such as $Ir(ppy)_3$; a blue phosphorescence emitting substance such as Flrpic or Flr6; or a red phosphorescence emitting substance such as $Btp_2Ir$ (acac) can be used. These phosphorescence emitting substances can be used by being doped in a hole injecting/transporting host material or an electron transporting host material. As the hole injecting/transporting host material, the following materials can be used in addition to the benzopyridoindole derivative of the present invention:

carbazole derivatives, for example,
4,4'-di (N-carbazolyl)biphenyl (hereinafter abbreviated as CBP);
TCTA; and
mCP.

Examples of the electron transporting host material are as follows:
p-bis(triphenylsilyl)benzene (hereinafter abbreviated as UGH2); and
2,2',2"-(1,3,5-phenylene)-tris(1-phenyl-1H-benzimidazole) (hereinafter abbreviated as TPBI).

By using any such material, a high performance organic EL element can be prepared.

Doping of the host material with the phosphorescent light emitting material is preferably performed by codeposition in a range of 1 to 30% by weight based on the entire light emission layer in order to avoid concentration quenching.

Also, a material which emits delayed fluorescence, such as a CDCB derivative, for example, PIC-TRZ, CC2TA, PXZ-TRZ, or 4CzIPN, can be used as the luminescent material.

The hole blocking layer 6 can be formed using a publicly known compound having hole blocking properties, aside from the benzopyridoindole derivative of the present invention. The publicly known compound having the hole blocking properties can be exemplified by the following:

Phenanthroline derivatives, for example, bathocuproine (hereinafter abbreviated as BCP);
Metal complexes of quinolinol derivatives, for example, BAlq;
Various rare earth complexes;
Oxazole derivatives;
Triazole derivatives; and
Triazine derivatives.

The hole blocking layer can also have a single-layer structure or a multilayer laminated structure, and each layer is formed using the benzopyridoindole derivative of the present invention or one or more of the aforementioned compounds having hole blocking action.

The benzopyridoindole derivative of the present invention and the above-mentioned publicly known material having the hole blocking action can also be used for the formation of the electron transport layer 7 to be described blow. That is, the layer concurrently serving as the hole blocking layer 6 and the electron transport layer 7 can be formed by using the benzopyridoindole derivative of the present invention or the above-mentioned publicly known material having the hole blocking action.

The electron transport layer 7 is formed using a publicly known compound having electron transporting properties, aside from the benzopyridoindole derivative of the present invention. The publicly known compound having the electron transporting properties can be exemplified by the following:

metal complexes of quinolinol derivatives including $Alq_3$ and BAlq;
various metal complexes;
triazole derivatives;
triazine derivatives;
oxadiazole derivatives;
pyridine derivatives;
pyrimidine derivatives;
benzimidazole derivatives;
thiadiazole derivatives;
anthracene derivatives;
carbodiimide derivatives;
quinoxaline derivatives;
pyridoindole derivatives;
phenanthroline derivatives; and
silole derivatives.

The electron transport layer can also have a single-layer structure or a multilayer laminated structure, and each layer is formed using the benzopyridoindole derivative of the present invention or one or more of the aforementioned compounds having electron transporting action.

The electron injection layer 8 can also be formed using the benzopyridoindole derivative of the present invention or a compound publicly known per se, for example, alkali metal salts such as lithium fluoride and cesium fluoride;

alkaline earth metal salts such as magnesium fluoride;

metal complexes of quinolinol derivatives such as lithium quinolinol; and metal oxides such as aluminum oxide. Upon preferred selection of the electron transport layer and the cathode, the electron injection layer can be omitted.

In the electron injection layer 8 or the electron transport layer 7, moreover, the material to be usually used for the layer is further N-doped with a metal such as cesium, and can be used for the layer.

In connection with the cathode 9, either an electrode material with a low work function such as aluminum, or an alloy having a lower work function, such as a magnesium-silver alloy, a magnesium-indium alloy, or an aluminum-magnesium alloy, is used as an electrode material.

EXAMPLES

The present invention will be described more concretely by way of Examples, but the present invention is in no way limited to the following Examples.

Example 1

Synthesis of Compound 3

Synthesis of 5-{9,10-di(naphthalen-2-yl)anthracen-2-yl}-11-phenyl-11H-benzo[g]pyrido[4,3-b]indole The mixture was heated, and stirred for 8.5 hours under reflux. The mixture was cooled to room temperature, and 30 ml of methanol and 30 ml of water were added. The mixture was stirred, and a crude product precipitated was collected by filtration. The crude product was purified by column chromatography (carrier: NH silica gel, eluent: toluene) to obtain 4.8 g (yield 62%) of 5-{9,10-di(naphthalen-2-yl)anthracen-2-yl}-11-phenyl-11H-benzo[g]pyrido[4,3-b]indole (Compound 3) as a yellow powder.

In connection with the resulting yellow powder, its structure was identified using NMR. The results of its $^1$H-NMR measurement are shown in FIG. 1. In $^1$H-NMR (THF-d$_8$), the following signals of 34 hydrogens were detected:

δ (ppm)=9.35(1H)
8.38 (1H)
8.25 (1H)
8.19 (1H)
8.12 (1H)
8.09 (1H)
8.07 (2H)
8.01 (1H)
7.99 (1H)
7.97 (1H)
7.92 (2H)
7.90 (1H)
7.80-7.78 (1H)
7.77-7.75 (1H)
7.73-7.65 (5H)
7.63-7.60 (2H)
7.58-7.54 (3H)
7.50-7.48 (2H)
7.46 (1H)
7.36-7.33 (3H)
7.16 (1H)
7.01 (1H)

(Compound 3)

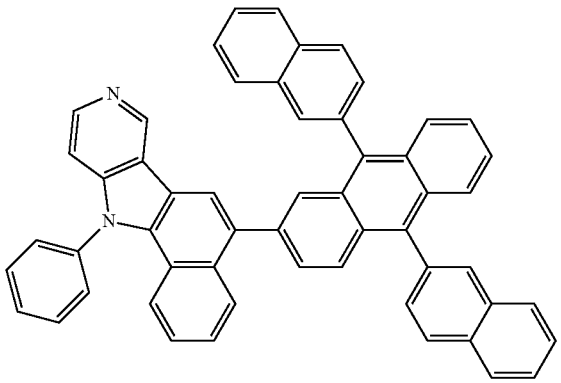 [SMILES: c1ccc(-n2c3ccncc3c3cc(-c4ccc5c(-c6ccc7ccccc7c6)c6ccccc6c(-c6ccc7ccccc7c6)c5c4)c4ccccc4c32)cc1]

| | |
|---|---|
| A nitrogen-purged reaction vessel was charged with | |
| 5-bromo-11-phenyl-11H-benzo[g]pyrido[4,3-b]indole | 4.0 g, |
| 9,10-di(naphthalen-2-yl)anthracen-2-ylboronic acid | 5.6 g, |
| tetrakis(triphenylphosphine)palladium | 0.6 g, |
| 2M aqueous solution of potassium carbonate | 15 ml, |
| toluene | 60 ml and |
| ethanol | 15 ml. |

A = single bond
Y = nitrogen atom

Example 2

Synthesis of Compound 55

Synthesis of 5-{4-(10-phenyl-anthracen-9-yl) phenyl}-11-phenyl-11H-benzo[g]pyrido[4,3-b]indole

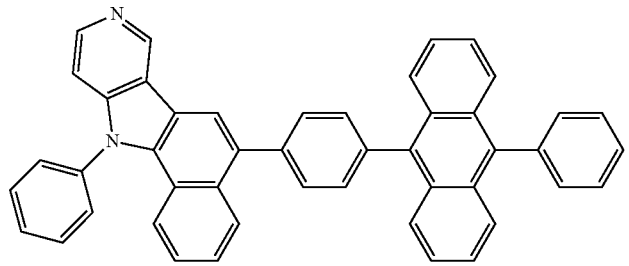 [SMILES: c1ccc(-c2c3ccccc3c(-c3ccc(-c4cc5c6cnccc6n(-c6ccccc6)c5c5ccccc45)cc3)c3ccccc23)cc1]
(Compound 55)

| | | |
|---|---|---|
| A nitrogen-purged reaction vessel was charged with | 4.0 g, | |
| 5-bromo-11-phenyl-11H-benzo[g]pyrido[4,3-b]indole | | |
| 4,4,5,5-tetramethyl-2-{4-(10-phenyl-anthracen-9-yl) phenyl}-[1,3,2]dioxaborane | 5.4 g, | |
| tetrakis(triphenylphosphine)palladium | 0.1 g, | |
| 2M aqueous solution of potassium carbonate | 15 ml, | |
| toluene | 60 ml and | |
| ethanol | 15 ml. | |

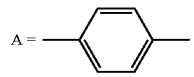

Y = nitrogen atom

The mixture was heated, and stirred for 7 hours under reflux. The mixture was cooled to room temperature, and 30 ml of water was added. The mixture was stirred, and an organic layer was collected by liquid separation. The organic layer was dehydrated over anhydrous magnesium sulfate, and then concentrated under reduced pressure to obtain a crude product. The crude product was purified by column chromatography (carrier: NH silica gel, eluent: toluene/hexane) to obtain 6.1 g (yield 92.4%) of 5-{4- (10-phenyl-anthracen-9-yl)phenyl}-11-phenyl-11H-benzo[g]pyrido[4,3-b]indole (Compound 55) as a light yellow powder.

Figure 2:
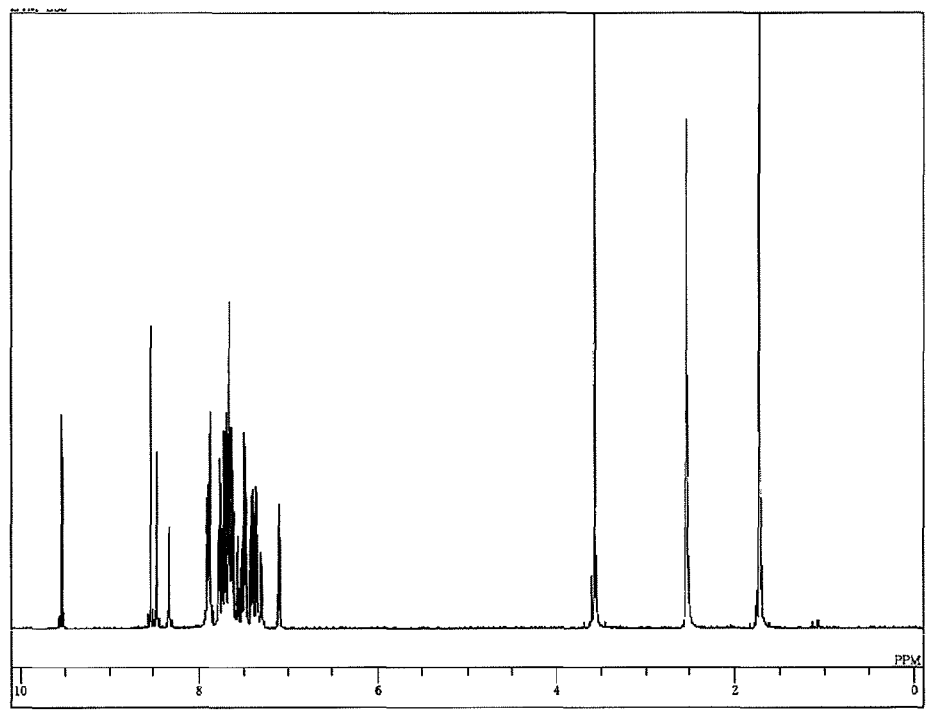
[FIG. 2] is a $^1$H-NMR chart diagram of the compound of Example 2 (Compound 55).

In connection with the resulting light yellow powder, its structure was identified using NMR. The results of its $^1$H-NMR measurement are shown in FIG. 2. In $^1$H-NMR (THF-d$_8$), the following signals of 30 hydrogens were detected:

δ (ppm)=9.54 (1H)
8.54 (1H)
8.47 (1H)
8.33 (1H)
7.90 (2H)
7.88 (2H)
7.80-7.61 (12H)
7.57 (1H)
7.52 (1H)
7.50 (2H)
7.42 (2H)
7.37 (2H)
7.30 (1H)
7.11 (1H)

<Measurements of Melting Point and Glass Transition Point>

The benzopyridoindole derivatives of the present invention obtained in the foregoing Examples were measured for the melting point and the glass transition point by a high sensitivity differential scanning calorimeter (DSC3100S, produced by Bruker AXS).

| | Melting point | Glass transition point |
|---|---|---|
| Compound of Example 1 | 339° C. | 203° C. |
| Compound of Example 2 | 215° C. | 178° C. |

The benzopyridoindole derivatives of the present invention have a glass transition point of 100° C. or higher, particularly, 170° C. or higher, demonstrating that the compounds of the present invention are stable in a thin film state. Furthermore, the benzopyridoindole derivatives of the present invention have a high melting point, excellent vapor deposition properties, and the advantage of easy handling.

<Measurement of Work Function>

Using each of the benzopyridoindole derivatives of the present invention obtained in the above Examples, a vapor deposited film with a film thickness of 100 nm was prepared on an ITO substrate, and its work function was measured using an ionization potential measuring device (PYS-202, produced by Sumitomo Heavy Industries, Ltd.).

| | Work function |
|---|---|
| Compound of Example 1 | 5.94 eV |
| Compound of Example 2 | 5.98 eV |

The benzopyridoindole derivatives of the present invention showed higher values than the work function of 5.5 eV shown by general hole transport materials such as NPD and TPD, and are thus found to have great hole blocking capability.

Evaluation of Organic EL Element Characteristics

Example 3

A hole injection layer 3, a hole transport layer 4, a light emission layer 5, a hole blocking layer 6, an electron transport layer 7, an electron injection layer 8, and a cathode (aluminum electrode) 9 were vapor deposited in this order on an ITO electrode formed beforehand as a transparent anode 2 on a glass substrate 1 to prepare an organic EL element as shown in FIG. 3.

Concretely, the glass substrate 1 having a 150 nm thick ITO film formed thereon was cleaned with an organic solvent, and then cleaned on the surface by oxygen plasma treatment. Then, the ITO electrode-equipped glass substrate was mounted within a vacuum deposition machine, and the pressure was reduced to 0.001 Pa or lower to form the transparent anode 2. Then, a film of Compound 78 represented by a structural formula indicated below was formed at a vapor deposition rate of 6 nm/min in a film thickness of 20 nm as the hole injection layer 3 so as to cover the transparent anode 2. On the hole injection layer 3, a film of Compound 79 represented by a structural formula indicated below was formed at a vapor deposition rate of 6 nm/min in a film thickness of 40 nm as the hole transport layer 4. On the hole transport layer 4, Compound 80 of the following structural formula and Compound 81 of the following structural formula were binary vapor deposited at such vapor deposition rates that the vapor deposition rate ratio was Compound 80:Compound 81=5:95, whereby the light emission layer 5 was formed in a film thickness of 30 nm. On this light emission layer 5, films of the compound of Example 1 (Compound 3) were formed at a vapor deposition rate of 6 nm/min in a film thickness of 30 nm as the hole blocking layer 6 and the electron transport layer 7. On the hole blocking layer 6 and the electron transport layer 7, a film of lithium fluoride was formed at a vapor deposition rate of 0.6 nm/min in a film thickness of 0.5 nm as the electron injection layer 8. Finally, aluminum was vapor deposited to a film thickness of 150 nm to form the cathode 9. The resulting organic EL element was measured for the light emission characteristics when a direct current voltage was applied at normal temperature in the atmosphere. The results of the measurements are shown in Table 1.

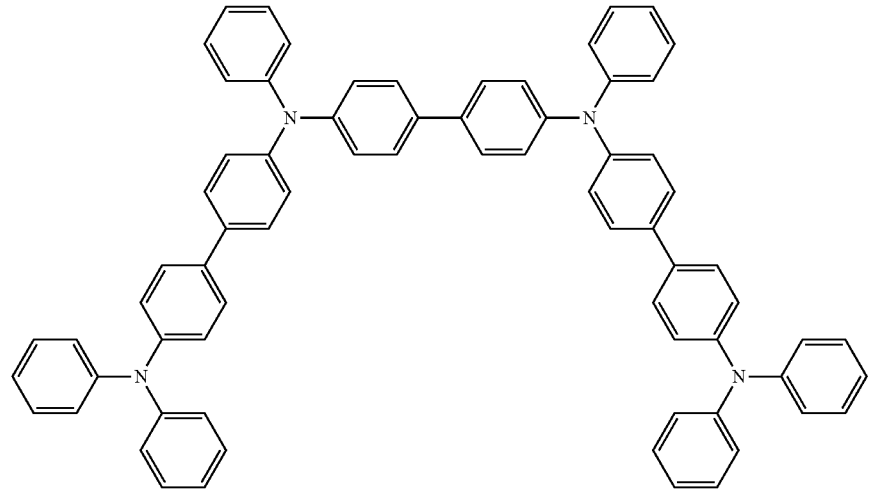

(Compound 78)

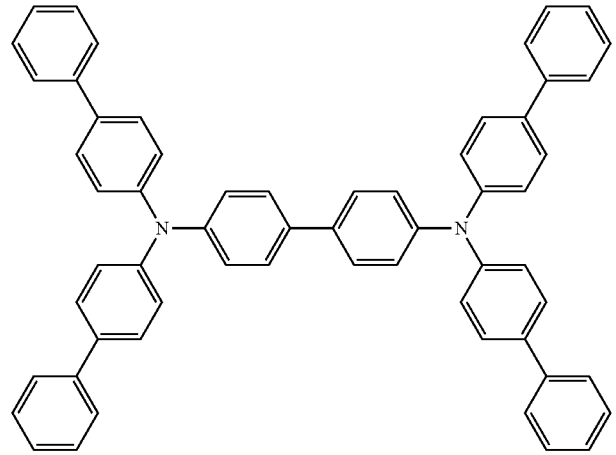

(Compound 79)

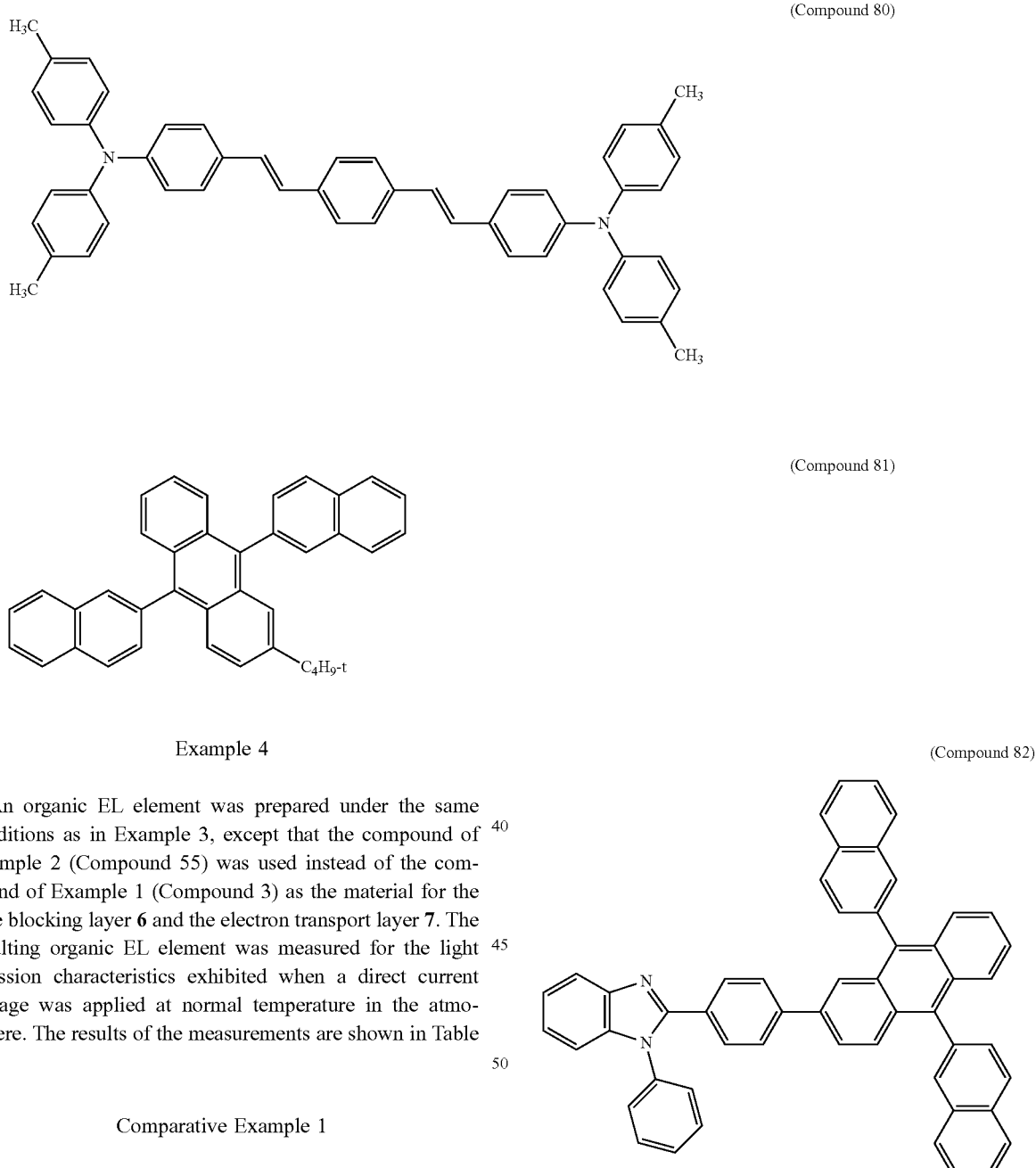

Example 4

An organic EL element was prepared under the same conditions as in Example 3, except that the compound of Example 2 (Compound 55) was used instead of the compound of Example 1 (Compound 3) as the material for the hole blocking layer 6 and the electron transport layer 7. The resulting organic EL element was measured for the light emission characteristics exhibited when a direct current voltage was applied at normal temperature in the atmosphere. The results of the measurements are shown in Table 1.

Comparative Example 1

For comparison, an organic EL element was prepared under the same conditions as in Example 3, except that Compound 82 (see Patent Document 5) of the following structural formula was used instead of the compound of Example 1 (Compound 3) as the material for the hole blocking layer 6 and the electron transport layer 7. The resulting organic EL element was measured for the light emission characteristics exhibited when a direct current voltage was applied at normal temperature in the atmosphere. The results of the measurements are shown in Table 1.

TABLE 1

| Compound | | *1 | *2 | *3 | *4 |
|---|---|---|---|---|---|
| Ex. 3 | Comp. 3 | 5.23 | 856 | 8.56 | 5.14 |
| Ex. 4 | Comp. 55 | 5.41 | 878 | 8.78 | 5.10 |
| Comp. Ex. 1 | Comp. 82 | 5.95 | 792 | 7.92 | 4.19 |

*1: Voltage [V] (@10 mA/cm$^2$)
*2: Luminance [cd/m$^2$] (@10 mA/cm$^2$)
*3: Luminous efficiency [cd/A] (@10 mA/cm$^2$)
*4: Power efficiency [lm/W] (@10 mA/cm$^2$)

As shown in Table 1, the driving voltage when an electric current at a current density of 10 mA/cm$^2$ was flowed showed low values of 5.23 to 5.41V in the organic EL elements of Example 3 and Example 4, as compared with 5.95V in the organic EL element of Comparative Example 1 using Compound 82. The luminance was 792 cd/m$^2$ in the organic EL element of Comparative Example 1, whereas the luminances were 856 to 878 cd/m$^2$ in the organic EL elements of Examples 3 and 4. The luminous efficiency was 7.92 cd/A in the organic EL element of Comparative Example 1, while those in the organic EL elements of Examples 3 and 4 were 8.56 to 8.78 cd/A. The power efficiency in the organic EL element of Comparative Example 1 was 4.19 lm/W, while those in the organic EL elements of Examples 3 and 4 were 5.10 to 5.14 lm/W. In all of the above parameters, the organic EL elements of Examples 3 and 4 were greatly improved over the organic EL element of Comparative Example 1.

The light emission starting voltage was measured using each of the organic EL elements obtained in Examples 3, 4 and Comparative Example 1. The results of the measurements are shown below.

| Organic EL element | Compound | Light emission starting voltage [V] |
| --- | --- | --- |
| Example 3 | Compound 3 | 2.8 |
| Example 4 | Compound 55 | 2.8 |
| Comparative Example 1 | Compound 82 | 3.1 |

In comparison with the organic EL element of Comparative Example 1 using Compound 82, the organic EL elements of Examples 3 and 4 were found to lower the light emission starting voltage.

As shown above, the organic EL elements of the present invention were found to be excellent in the luminous efficiency and the power efficiency, and be capable of achieving marked decreases in the practical driving voltage, in comparison with the organic EL element using Compound 82 used as a general electron transport material.

INDUSTRIAL APPLICABILITY

The benzopyridoindole derivative of the present invention is satisfactory in electron injection properties, excellent in hole blocking capability, superior in heat resistance, and stable in a thin film state, so that it excels as a compound for an organic EL element. By preparing an organic EL element with the use of this compound, high efficiencies can be obtained, the driving voltage can be lowered, and the durability can be improved. The resulting organic EL element can be put to uses such as domestic electrical appliances and illumination. EXPLANATIONS OF LETTERS OR NUMERALS 1 Glass substrate
2 Transparent anode
3 Hole injection layer
4 Hole transport layer
5 Light emission layer
6 Hole blocking layer
7 Electron Transport layer
8 Electron injection layer
9 Cathode

The invention claimed is:
1. A benzopyridoindole derivative represented by the following general formula (1)

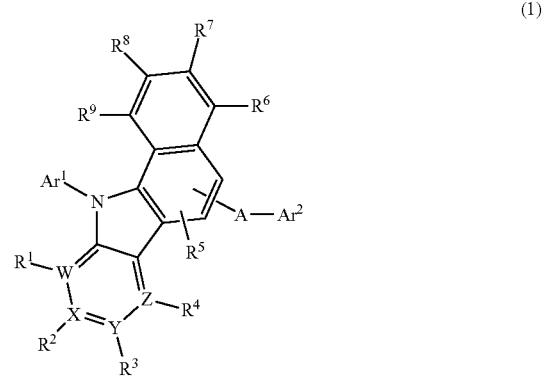

(1)

wherein,
A represents a single bond, a divalent group of an aromatic hydrocarbon, a divalent group of an aromatic heterocycle, or a divalent group of a condensed polycyclic aromatic,
$Ar^1$ and $Ar^2$ may be the same or different, and each represent an aromatic hydrocarbon group, an aromatic heterocyclic group, or a condensed polycyclic aromatic group,
$R^1$ to $R^9$ may be the same or different, and each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group,
W, X, Y and Z each represent a carbon atom or a nitrogen atom, and
only one of W, X, Y and Z is a nitrogen atom, and the nitrogen atom does not have the hydrogen atom of $R^1$ to $R^4$ or a substituent.

2. The benzopyridoindole derivative according to claim 1 which is represented by the following general formula (1-1):

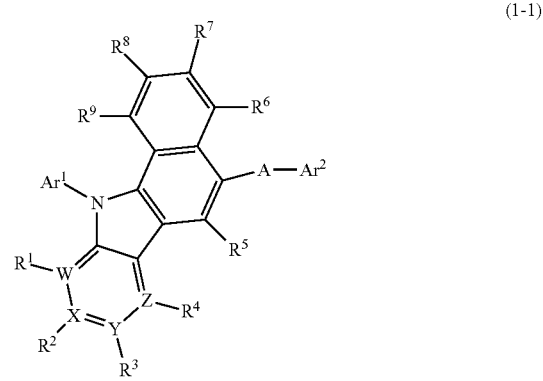

(1-1)

wherein,
A, $Ar^1$, $Ar^2$ $R^1$ to $R^9$, W, X, Y and Z have the same meanings as those defined for the general formula (1).

3. The benzopyridoindole derivative according to claim 1, wherein A is a single bond.

4. The benzopyridoindole derivative according to claim 1, wherein A is a divalent group of an aromatic hydrocarbon having one or two rings, or a divalent group of naphthalene.

5. The benzopyridoindole derivative according to claim 1, wherein $Ar^2$ is an aromatic hydrocarbon group having 3 or more rings, or a tri- or higher cyclic condensed polycyclic aromatic group.

6. The benzopyridoindole derivative according to claim 5, wherein $Ar^2$ is an anthracenyl group having a substituent.

7. The benzopyridoindole derivative according to claim 1, wherein $Ar^1$ is an unsubstituted phenyl group.

8. An organic electroluminescent element including a pair of electrodes and at least one organic layer sandwiched therebetween, wherein the benzopyridoindole derivative according to claim 1 is used as a constituent material for the at least one organic layer.

9. The organic electroluminescent element according to claim 8, wherein the organic layer is an electron transport layer.

10. The organic electroluminescent element according to claim 8, wherein the organic layer is a hole blocking layer.

11. The organic electroluminescent element according to claim 8, wherein the organic layer is a light emission layer.

12. The organic electroluminescent element according to claim 8, wherein the organic layer is an electron injection layer.

* * * * *

UNITED STATES PATENT AND TRADEMARK OFFICE
CERTIFICATE OF CORRECTION

PATENT NO. : 9,837,620 B2
APPLICATION NO. : 14/913774
DATED : December 5, 2017
INVENTOR(S) : Nagaoka et al.

Page 1 of 1

It is certified that error appears in the above-identified patent and that said Letters Patent is hereby corrected as shown below:

In the Claims

Column 54, Line 65 Claim 2, please change "A, $Ar^{t'}$" to -- A, $Ar^1$ --

Signed and Sealed this
Twenty-fourth Day of July, 2018

Andrei Iancu
*Director of the United States Patent and Trademark Office*